US012738346B2

(12) United States Patent
Liu et al.

(10) Patent No.: US 12,738,346 B2
(45) Date of Patent: Sep. 15, 2026

(54) USING NEURAL NETWORKS TO PREDICT PEPTIDE IMMUNOGENICITY

(71) Applicant: Genentech, Inc., South San Francisco, CA (US)

(72) Inventors: Kai Liu, Belmont, CA (US); Milad Salem, Orlando, FL (US); William John Thrift, San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 236 days.

(21) Appl. No.: 18/472,669

(22) Filed: Sep. 22, 2023

(65) Prior Publication Data

US 2024/0021274 A1 Jan. 18, 2024

Related U.S. Application Data

(63) Continuation of application No. PCT/US2022/022037, filed on Mar. 25, 2022.

(Continued)

(51) Int. Cl.

*G16B 40/20* (2019.01)
*G16B 20/00* (2019.01)

(Continued)

(52) U.S. Cl.

CPC ............. *G16B 40/20* (2019.02); *G16B 20/00* (2019.02); *G16H 15/00* (2018.01); *G16H 20/10* (2018.01)

(58) Field of Classification Search

None

See application file for complete search history.

(56) References Cited

U.S. PATENT DOCUMENTS

2010/0111993 A1 5/2010 Tuereci et al.
2010/0129877 A1 5/2010 Sahin et al.

(Continued)

FOREIGN PATENT DOCUMENTS

JP 2019-518295 A 6/2019
JP 2020-523010 A 8/2020

(Continued)

OTHER PUBLICATIONS

Shao et al. ("High-Throughput Prediction of MHC Class I and II Neoantigens with MHCnuggets", Cancer Immunology Research, vol. 8, No. 3, Dec. 23, 2019, pp. 396-408) (Year: 2019).*

(Continued)

*Primary Examiner* — Christopher B Tokarczyk

(74) *Attorney, Agent, or Firm* — MORRISON & FOERSTER LLP

(57) ABSTRACT

Methods, systems, compositions, and computer program products are provided for accurately identifying candidate neoantigens that exhibit immunogenic properties. In some embodiments, a method provided herein includes receiving a set of candidate peptide sequences, each candidate peptide sequence in the set having a major histocompatibility complex (MHC) presentation score meeting a pre-set criterion. The method further includes identifying a corresponding MHC peptide sequence associated with each candidate peptide sequence in the set; generating immunogenicity input vectors from the set of candidate peptide sequences by processing a representation of each candidate peptide sequence in the set of candidate peptide sequences and a representation of the corresponding MHC peptide sequence for each candidate peptide sequence in the set. The method further includes inputting the immunogenicity input vectors into an immunogenicity model to generate predictions of (Continued)

whether a candidate peptide sequence in the set is immunogenic; and returning an output comprising the predictions.

20 Claims, 9 Drawing Sheets

Related U.S. Application Data

(60) Provisional application No. 63/166,030, filed on Mar. 25, 2021.

(51) Int. Cl.
*G16H 15/00* (2018.01)
*G16H 20/10* (2018.01)

(56) References Cited

U.S. PATENT DOCUMENTS

| | | | | |
|---|---|---|---|---|
| 2019/0259474 | A1* | 8/2019 | Wang | G16B 40/20 |
| 2020/0243164 | A1 | 7/2020 | Qiao et al. | |
| 2021/0098077 | A1* | 4/2021 | Yelensky | G01N 33/57484 |
| 2021/0104294 | A1 | 4/2021 | Hacohen et al. | |
| 2021/0375393 | A1* | 12/2021 | Bremel | G16B 20/00 |
| 2022/0122690 | A1 | 4/2022 | Liu et al. | |
| 2022/0154281 | A1* | 5/2022 | Boucher | C12Q 1/6886 |
| 2025/0273294 | A1 | 8/2025 | Cui et al. | |
| 2026/0018244 | A1 | 1/2026 | Jhunjhunwala et al. | |

FOREIGN PATENT DOCUMENTS

| | | | |
|---|---|---|---|
| WO | 2003104803 | A2 | 12/2003 |
| WO | 2005038030 | A1 | 4/2005 |
| WO | 2007036366 | A2 | 4/2007 |
| WO | 2011015347 | A1 | 2/2011 |
| WO | 2013143683 | A1 | 10/2013 |
| WO | 2017060314 | A2 | 4/2017 |
| WO | 2019161342 | A1 | 8/2019 |
| WO | 2020046587 | A2 | 3/2020 |
| WO | 2020132586 | A1 | 6/2020 |
| WO | 2020/234188 | A1 | 11/2020 |
| WO | 2022016125 | A1 | 1/2022 |
| WO | 2024107754 | A1 | 5/2024 |
| WO | 2024123699 | A1 | 6/2024 |

OTHER PUBLICATIONS

Caron, E. et al. (Oct. 19, 2015). "Analysis of Major Histocompatibility Complex (MHC) Immunopeptides Using Mass Spectroscopy," Molecular and Cellular Proteomics 14(12):3105-3117.
Devlin, J. et al. (Oct. 11, 2018). "BERT: Pretraining of Deep Bidirectional Transformers for Language Understanding," arXiv, 16 pages.
German, M. A. et al. (Aug. 2008). "Global Identification of MicroRNA-Target RNA Pairs by Parallel Analysis of RNA Ends," Nature Biotechnology 26(8):941-946.
International Search Report and Written Opinion, mailed Jul. 19, 2022, for PCT Application No. PCT/US2022/022037, filed Mar. 25, 2022, 17 pages.
Kim, S. et al. (Apr. 1, 2018, e-pub. Jan. 19, 2018). "Neopepsee: Accurate Genome-Level Prediction of Neoantigens by Harnessing Sequence and Amino Acid Immunogenicity Information," Annals of Oncology 29 (4):1030-1036.
Ozsolak, F. et al. (Feb. 2011, e-pub. Dec. 30, 2010). "RNA Sequencing: Advances, Challenges and Opportunities," Nature Reviews 12:87-98.
Rao, R. et al. (Dec. 2019). "Evaluating Protein Transfer Learning with TAPE," Adv. in Neural Information Processing Sys. 32:9689-9701, 20 pages.
Romero, M. et al. (Dec. 17, 2019). "Training Deep Learning Models with Small Datasets," Accurate Decision Trees View Project, 20 pages.
Shao, X.M. et al. (Mar. 2020, e-pub. Dec. 23, 2019). "High-Throughput Prediction of MHC Class I and II Neoantigens with MHCnuggets," Cancer Immunology Research 8(3):396-408.
Tang, F. et al. (May 2009, e-pub. Apr. 2009). "mRNA-Seq Whole-Transcriptome Analysis of a Single Cell," Nature Methods 6(5):377-382.
Wang, Z. et al. (Jan. 2009, e-pub. Nov. 18, 2008). "RNA-Seq: A Revolutionary Tool for Transcriptomics," Nature Reviews 10:57-63.
Wittman, V.P. et al. (2006). "Antibody Targeting to a Class I MHC-Peptide Epitope Promotes Tumor Cell Death," J. of Immunol. 177:4187-4195.
Xu, C. (2018, e-pub. Feb. 6, 2018). "A Review of Somatic Single Nucleotide Variant Calling Algorithms for next-Generation Sequencing Data," Comput. Struct. Biotechnol. J. 16:15-24.
International Preliminary Report on Patentability, issued Sep. 12, 2023, for PCT Application No. PCT/US2022/022037, filed Mar. 25, 2022, 12 pages.
Rives, A. et al. (Dec. 15, 2020). "Biological Structure and Function Emerge from Scaling Unsupervised Learning to 250 Million Protein Sequences," bioRxiv, 46 pages.
Cieślik, M et al. (Feb. 2018, e-pub. Dec. 27, 2017). "Cancer Transcriptome Profiling at the Juncture of Clinical Translation," Nature Reviews: Genetics 19:93-109, 17 pages.
De Simone, M. et al. (Jul. 18, 2018). "Single Cell T Cell Receptor Sequencing: Techniques and Future Challenges," Front. Immunol. 9(1638):1-7.
Hu, Y. et al. (2019, e-pub. May 23, 2019). "ACME: Pan-Specific Peptide-MHC Class I Binding Prediction Through Attention-Based Deep Neural Networks," Bioinformatics 35(23):4946-4954.
International Preliminary Report on Patentability, issued Apr. 29, 2025, for PCT Application No. PCT/US2023/079683, filed on Nov. 14, 2023, 19 pages.
International Preliminary Report on Patentability, issued Jan. 17, 2023, for PCT Application No. PCT/US2021/042105, filed Jul. 16, 2021, 10 pages.
International Preliminary Report on Patentability, issued Jun. 10, 2025, for PCT Application No. PCT/US2023/082356, filed Dec. 4, 2023, 15 pages.
International Search report and Written Opinion mailed on Mar. 18, 2024, for PCT Application No. PCT/US2023/079683, filed on Nov. 14, 2023, 22 pages.
International Search Report and Written Opinion, mailed May 21, 2024, for PCT Application No. PCT/US2023/082356, filed Dec. 4, 2023, 21 pages.
International Search Report and Written Opinion, mailed Oct. 29, 2021, for PCT Application No. PCT/US2021/042105, filed Jul. 16, 2021, 13 pages.
Jurtz, V. et al. (2017, e-pub. Oct. 4, 2017). "NetMHCpan-4.0: Improved Peptide-MHC Class I Interaction Predictions Integrating Eluted Ligand and Peptide Binding Affinity Data," J Immunol. 199:3360-3368.
Matsuda, T. et al. (Nov. 1, 2018). "Induction of Neoantigen-Specific Cytotoxic T Cells and Construction of T-cell Receptor Engineered T Cells for Ovarian Cancer," Clin. Cancer Res. 24(21):5357-5367.
Phloyphisut, P. et al. (2018, e-pub. Jul. 18, 2018). "MHCSeqNet: A Deep Neural Network Model for Universal MHC Binding Prediction," bipoRxiv, 14 pages.
Sidhom, J.-W. et al. (Dec. 23, 2019). "DeepTCR: A Deep Learning Framework for Understanding T-Cell Receptor Sequence Signatures Within Complex T-Cell Repertoires," bioRxiv, 33 pages.
Vaswani, A. et al. (2017). "Attention is All You Need." 31st Conference on Neural Information Systems, 11 pages.
Venkatesh, G. et al. (2020). "MHCAttnNet: Predicting MHC-Peptide Bindings for MHCalleles Classes I and II Using an Attention-Based Deep Neural Model," Bioinformatics 36:i399-i406.
Wang, L. et al. (2019). "High-Throughput Sequence of CD4-+ T Cell Repertoire Reveals Disease-Specific Signatures in IgG4-Related Disease," Arthritis Research & Therapy 21:295, 15 pages.
Wu, J et al. (Nov. 1, 2019). "DeepHLApan: A Deep Learning Approach for Neoantigen Prediction Considering Both HLA-Peptide Binding and Immunogenicity," Frontiers in Immunology 10(2559):1-11.

(56) References Cited

OTHER PUBLICATIONS

You, R. et al. (Jun. 24, 2022). "DeepMHCII: A Novel Binding Core-Aware Deep Interaction Model for Accurate MHC-II Peptide Binding Affinity Prediction," Bioinformationics 38(Suppl. 1):i220-i228.
Zhang, A. et al. (Nov. 13, 2022). "Dive Into Deep Learning," arXiv.org, 1184 pages.
Zhu, G. et al. (Mar. 9, 2017). "Efficient Nanovaccine Delivery in Cancer Immunotherapy," ACS Nano 11:2387-2392.
Zong, S. et al. (Feb. 10, 2020). "Very Rapid Cloning, Expression and Identifying Specificity of T-Cell Receptors for T-Cell Engineering," PloS ONE 15(2):e0228112, 20 pages.

* cited by examiner

125 MHC I DATA

110 PRETRAINED IMMUNOGENICITY MODEL

130 MHC I TRAINING PROCESS

135 MHC II DATA

140 MHC II TRAINING PROCESS

145 IMMUNOGENICITY DATA

150 IMMUNOGENICITY TRAINING PROCESS

160 IMMUNOGENICITY MODEL

500

| | MODEL | P-VALUE | ROC-AUC |
|---|---|---|---|
| 510 | BASELINE (ZERO-SHOT MHC I) | **2E-6** | **0.682** |
| 520 | TAPE + IMMUNOGENICITY | 0.07 | 0.432 |
| 530 | TAPE + MHC I + IMMUNOGENICITY | 0.001 | 0.622 |
| 540 | TAPE + MHC I + MHC II + IMMUNOGENICITY | **3E-5** | **0.657** |

FIG. 5

USING NEURAL NETWORKS TO PREDICT PEPTIDE IMMUNOGENICITY

CROSS-REFERENCE TO RELATED APPLICATION

This application is a continuation of International Application No. PCT/US2022/022037, filed on Mar. 25, 2022, which claims the benefit of and priority to U.S. Provisional Application No. 63/166,030, entitled "USING NEURAL NETWORKS TO PREDICT PEPTIDE IMMUNOGENICITY," filed on Mar. 25, 2021, the disclosures of which are hereby incorporated by reference in their entirety for all purposes.

BACKGROUND

Provided herein are methods, compositions, program products, and systems for generating immunogenicity predictions for peptides of interest. More specifically, compositions, methods, systems, and computer program products are provided for predicting immunogenicity of peptides of interest using machine learning models and selecting and using peptides based on their predicted immunogenicity.

Neoantigen therapies, including, but not limited to, neoantigen vaccines or personalized T-cell therapeutics, are a relatively new approach for providing individualized cancer treatment. Neoantigens are tumor-specific antigens that are derived from somatic mutations in tumors and are presented by a subject's cancer cells and antigen presenting cells.

Neoantigen vaccines can prime a subject's T cells to recognize and attack cancer cells expressing one or more particular tumor neoantigens. This approach generates a tumor-specific immune response that spares healthy cells while targeting tumor cells. The individualized vaccine may be engineered or selected based on a subject-specific tumor profile. The tumor profile can be defined by determining DNA and/or RNA sequences from a subject's tumor cell and using these sequences to identify neoantigens of interest that are present in tumor cells but absent in normal cells and that are made available on the surface of tumor cells (presentation) so that they are available to provoke an immune response of suitable magnitude (high immunogenicity).

Thus, there remains a need for improved prediction methods and systems to accurately identify candidate neoantigens from tumor tissue that are both present on the surface of tumor cells and exhibit immunogenic properties to help select candidate neoantigens that will be effective treatments against tumors.

SUMMARY

The embodiments described herein provide various compositions, methods, systems, and computer program products for accurately identifying candidate neoantigens that exhibit immunogenic properties.

In some embodiments, a method provided herein includes receiving a set of candidate peptide sequences, each candidate peptide sequence in the set having a major histocompatibility complex (MHC) presentation score meeting a pre-set criterion. The set of candidate peptide sequences is associated with a diseased sample of a subject. The MHC presentation score indicates a likelihood that a corresponding candidate peptide sequence in the set is presented by an MHC protein on a cell surface of the diseased sample. The method further includes identifying a corresponding MHC peptide sequence associated with each candidate peptide sequence in the set; generating immunogenicity input vectors from the set of candidate peptide sequences by processing a representation of each candidate peptide sequence in the set of candidate peptide sequences and a representation of the corresponding MHC peptide sequence for each candidate peptide sequence in the set. The method further includes inputting the immunogenicity input vectors into an immunogenicity model to generate predictions of whether a candidate peptide sequence in the set is immunogenic, a likelihood that a candidate peptide sequence in the set is immunogenic, or a combination thereof; and returning an output comprising the predictions.

In some embodiments, a method described herein includes receiving a candidate peptide sequence having a major histocompatibility complex (MHC) presentation score meeting a pre-set criterion, wherein the candidate peptide sequence is associated with a diseased sample of a subject, and wherein the MHC presentation score indicates a likelihood that the candidate peptide sequence is presented by an MHC protein on a cell surface of the diseased sample. The method further includes identifying a corresponding MHC peptide sequence associated with the candidate peptide sequence; generating an input vector for the candidate peptide sequence by processing a representation of the candidate peptide sequence and a representation of the corresponding MHC peptide sequence. The method further includes inputting the input vector generated into an immunogenicity model to generate a prediction of whether the candidate peptide sequence is immunogenic, a likelihood that the candidate peptide sequence is immunogenic, or a combination thereof; and returning an output comprising the prediction.

In some embodiments, a vaccine composition or a genetically engineered T cell composition provided herein includes one or more peptides, a plurality of nucleic acids that encode the one or more peptides, a plurality of cells expressing the one or more peptides, or a combination thereof, wherein the one or more peptides were selected from the set of candidate peptide sequences based on the predictions generated by performing part or all of one or more methods disclosed herein.

In some embodiments, a method of manufacturing a vaccine composition or a genetically engineered T cell provided herein includes producing a vaccine comprising one or more peptides, a plurality of nucleic acids that encode the one or more peptides, a plurality of cells expressing the one or more peptides, or a combination thereof, wherein the one or more peptides were selected from the set of candidate peptide sequences based on the predictions generated by performing part or all of one or more methods disclosed herein.

In some embodiments, a pharmaceutical composition provided herein includes one or more peptides having been selected from the set of candidate peptide sequences based on the predictions generated by performing part or all of one or more methods disclosed herein.

In some embodiments, a pharmaceutical composition provided herein includes a nucleic acid sequence that encodes one or more peptides having been selected from the set of candidate peptide sequences based on the predictions generated by performing part or all of one or more methods disclosed herein.

In some embodiments, a method of treating a subject described herein includes administering one or more peptides, one or more pharmaceutical compositions, or one or more nucleic acid sequences identified based on the predictions generated by performing part or all of one or more methods disclosed herein.

In some embodiments, a system is provided that includes one or more data processors and a non-transitory computer readable storage medium containing instructions which, when executed on the one or more data processors, cause the one or more data processors to perform part or all of one or more methods disclosed herein.

In some embodiments, a computer-program product is provided that is tangibly embodied in a non-transitory machine-readable storage medium and that includes instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the coneepts herein disclosed may be resorted to by those skilled in the art, and that such modifications and variations are considered to be within the scope of this invention as defined by the appended claims.

BRIEF DESCRIPTION OF THE DRAWINGS

The present disclosure is described in conjunction with the appended figures:

FIG. 5 is a table comparing different models for immunogenicity prediction in accordance with various embodiments.

Figure 1A:
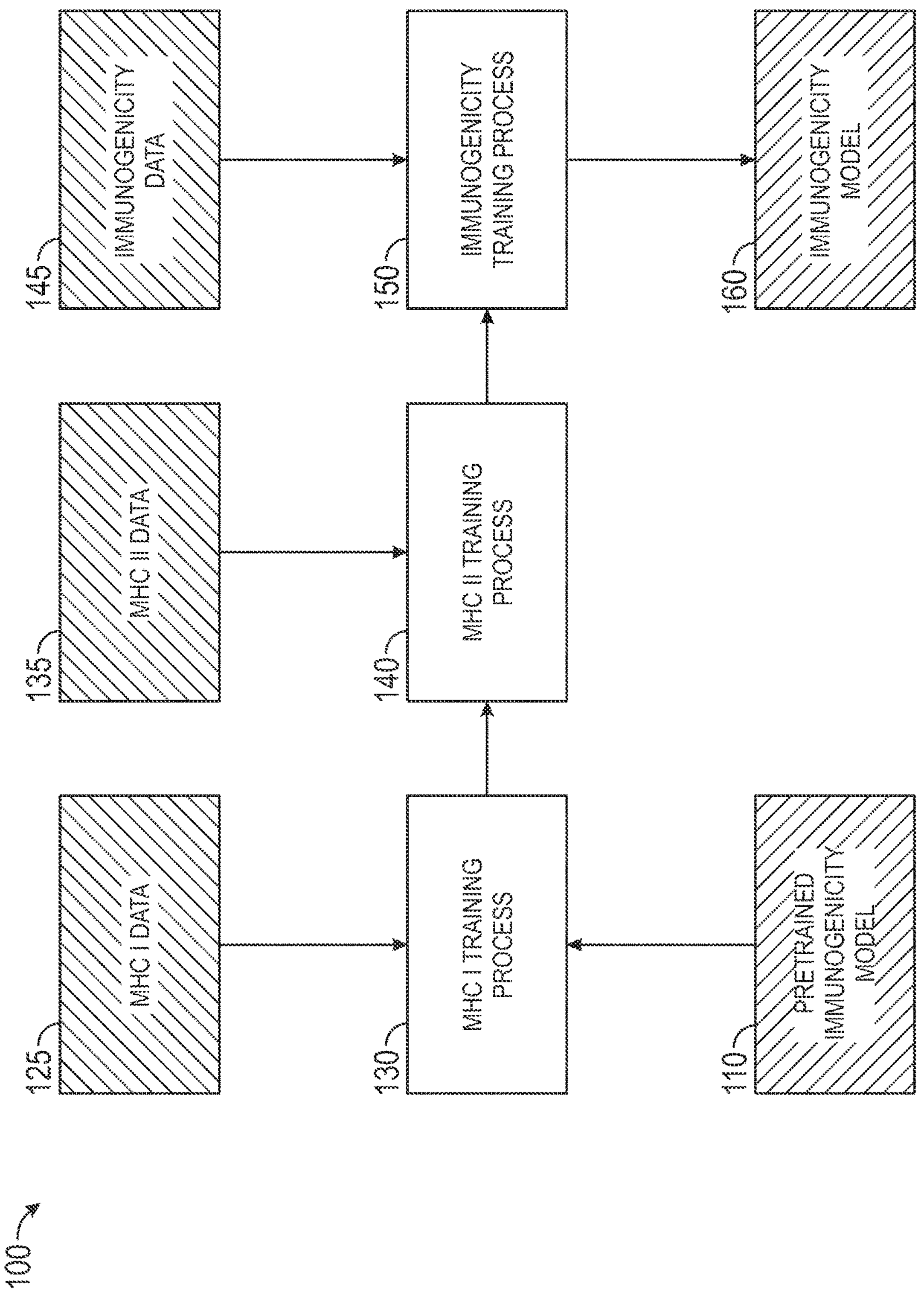
FIG. 1A is an illustration of a workflow for training an immunogenicity model to predict immunogenicity of neoantigen candidates in accordance with one or more embodiments.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

I. Overview

This disclosure describes various exemplary embodiments for accurately identifying candidate neoantigens from diseased samples that are both presented on the surface of tumor cells and exhibit immunogenic properties. The disclosure, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion.

I. Definitions

It is to be understood that the terminology used herein is for the purpose of describing particular embodiments only, and is not intended to be limiting.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Generally, nomenclatures utilized in connection with, and techniques of, chemistry, biochemistry, molecular biology, pharmacology and toxicology are described herein are those well-known and commonly used in the art.

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes," "including," "comprises," and/or "comprising" when used herein, specify the presence of stated features, integers, steps, operations, elements, components, and/or units but do not preclude the presence or addition of one or more other features, integers, steps, operations, elements, components, units, and/or groups thereof.

Throughout this disclosure, various aspects are presented in a range format. It should be understood that the description in range format is merely for convenience and brevity and should not be construed as an inflexible limitation on the disclosure. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed in the disclosure. The upper and lower limits of these smaller ranges may independently be included in the smaller ranges, and are also encompassed in the disclosure, subject to any specifically excluded limit in the stated range. Where the stated range includes one or both of the limits, ranges excluding either or both of those included limits are also included in the disclosure. This applies regardless of the breadth of the range.

The term "about" as used herein refers to include the usual error range for the respective value readily known. Reference to "about" a value or parameter herein includes (and describes) embodiments that are directed to that value or parameter per se. For example, description referring to "about X" includes description of "X." In some embodiments, "about" may refer to ±15%, ±10%, ±5%, or ±1% as understood by a person of skill in the art.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

As used herein, the term "ones" means more than one.

As used herein, the term "plurality" or "group" can be 2, 3, 4, 5, 6, 7, 8, 9, 10, or more.

As used herein, the term "set" means one or more.

As used herein, the phrase "at least one of," when used with a list of items, means different combinations of one or more of the listed items may be used and only one of the items in the list may be needed. The item may be a particular object, thing, step, operation, process, or category. In other words, "at least one of" means any combination of items or number of items may be used from the list, but not all of the items in the list may be required. For example, without limitation, "at least one of item A, item B, or item C" or "at least one of item A, item B, and item C" may mean item A; item A and item B; item B; item A, item B, and item C; item B and item C; or item A and C. In some cases, "at least one of item A, item B, or item C" or "at least one of item A, item B, and item C" may mean, but is not limited to, two of item A, one of item B, and ten of item C; four of item B and seven of item C; or some other suitable combination.

As used herein, a "subject" encompasses one or more cells, tissue, or an organism. The subject may be a human or non-human, whether in vivo, ex vivo, or in vitro, male or female. A subject can be a mammal, such as a human.

As used herein, the term "cell" is used interchangeably with the term "biological cell." Examples of biological cells include eukaryotic cells, plant cells, animal cells, such as mammalian cells, reptilian cells, avian cells, fish cells or the like, prokaryotic cells, bacterial cells, fungal cells, protozoan cells, or the like, cells dissociated from a tissue, such as muscle, cartilage, fat, skin, liver, lung, neural tissue, and the like, immunological cells, such as T cells, B cells, natural killer cells, macrophages, and the like, embryos (e.g., zygotes), oocytes, ova, sperm cells, hybridomas, cultured cells, cells from a cell line, cancer cells, infected cells, transfected and/or transformed cells, reporter cells and the like. A mammalian cell can be, for example, from a human, mouse, rat, horse, goat, sheep, cow, primate or the like.

A "nucleotide," "polynucleotide," "nucleic acid," or "oligonucleotide" refers to a linear polymer of nucleosides (including deoxyribonucleosides, ribonucleosides, or analogs thereof) joined by internucleosidic linkages. For example, a polynucleotide comprises at least three nucleosides. Usually, oligonucleotides range in size from a few monomeric units, e.g. 3-4, to several hundreds of monomeric units. The bases include adenine (A), cytosine (C), guanine (G), thymine (T), and uracil (U). The letters A, C, G, T, and U may be used to refer to the bases themselves, to nucleosides, or to nucleotides comprising the bases, as is standard in the art.

As used herein, the terms "peptide", "polypeptide" and "protein" are used interchangeably to refer to a polymer of amino acid residues. The terms encompass amino acid chains of any length, including full-length proteins with amino acid residues linked by covalent peptide bonds.

As used herein, an "epitope" of a peptide refers to a region of the peptide between the C-flank and N-flank and that is recognized by a T cell receptor (TCR). The epitope of the peptide is a part of the peptide that is recognized by TCR on a T cell and major histocompatibility complex (MHC) on an antigen presenting cell. For example, the epitope can be a peptide to which a TCR binds. For example, the epitope can be a peptide to which the TCR binds when the peptide is bound to MHC on an antigen presenting cell.

As used herein, a "ligand" is a peptide that is found to be presented by an MHC molecule at the cell surface as identified from elution experiments or is found to be bound to MHC as identified in an in vitro assay.

As used herein, "MHC" refers to a major histocompatibility complex. The human MHC is also called a human leukocyte antigen (HLA) complex. Each MHC molecule on the cell surface displays a small peptide (a molecular fraction of a protein) called an epitope. The presentation of pathogen-derived proteins results in the elimination of the infected cell by the immune system. MHC class I molecules are expressed in all nucleated cells and also in platelets—in essence all cells but red blood cells. MHC class I molecules present epitopes to killer T cells, also called cytotoxic T lymphocytes (CTLs). A CTL expresses CD8 receptors, in addition to T-cell receptors (TCR)s. MHC class II can be conditionally expressed by all cell types, but normally occurs only on "professional" antigen-presenting cells (APCs): macrophages, B cells, and especially dendritic cells (DCs). An APC takes up an antigenic protein, performs antigen processing, and returns a molecular fraction of the antigenic protein—a fraction termed the epitope—and displays the epitope on the APCs surface coupled within an MHC class II molecule (antigen presentation). On the cell's surface, the epitope can be recognized by immunologic structures like T-cell receptors (TCRs). The molecular region of an antibody, which binds to the epitope, is the paratope.

As used herein, a "mutant peptide" refers to a peptide that is not present in the wild type amino acid sequences of normal tissue of an individual subject. A mutant peptide comprises at least one mutant amino acid present in a disease tissue (e.g., collected from a particular subject) but not in a normal tissue (e.g., collected from the particular subject, collected from a different subject and/or as identified in a database as corresponding to normal tissue). A mutant peptide includes an epitope and thus is a substance that induces an immune response (as a result of not being associated with a subject's "self"). A mutant peptide can include and/or can be a neoantigen. A mutant peptide can arise from, for example: a non-synonymous mutation leading to different amino acids in the protein (e.g., point mutation); a read-through mutation in which a stop codon is modified or deleted, leading to translation of a longer protein with a novel tumor-specific sequence at the C-terminus; a splice site mutation that leads to a unique tumor-specific protein sequence; a chromosomal rearrangement that gives rise to a chimeric protein with a tumor-specific sequence at a junction of two proteins (i.e., gene fusion) and/or a frameshift insertion or deletion that leads to a new open reading frame with a tumor-specific protein sequence. A mutant peptide can include a polypeptide (as characterized by a polypeptide sequence) and/or may be encoded by a nucleotide sequence.

As used herein, a "C-flank" of a peptide refers to amino acids upstream of the C-terminus of a ligand, from the parent protein. Optionally, a C-flank of a peptide includes one, two, three, four, five or more amino acid residues upstream of C-terminal end of the peptide.

As used herein, an "N-flank" of a peptide refers to amino acids downstream of the N-terminus of a ligand, from the parent protein. Optionally, an N-flank of a peptide includes one, two, three, four, five or more amino acid residues downstream of the N-terminal end of the peptide.

As used herein, a "sequence" of a peptide or portion of a peptide refers to an amino-acid sequence that includes an ordered set of amino-acid identifiers.

As used herein, a "reference sequence" refers to a sequence that identifies amino acids within at least part of a non-mutant peptide or wild-type peptide (e.g., wild-type, parental sequence). The non-mutant or wild-type peptide may include no variants or fewer variants than included in a mutant peptide identified by a variant-coding sequence. The reference sequence may include an amino-acid sequence encoded by a genetic sequence within a same gene relative to a gene that includes a corresponding variant-coding sequence. The reference sequence may include an amino-acid sequence encoded by a genetic sequence spanning a same start and stop within a gene relative to intra-gene positions associated with a genetic sequence associated with a corresponding variant-coding sequence. The reference sequence may be identified by collecting a non-disease and/or non-tumor sample from one or more subjects (who may, but need not, include a subject from which a diseased sample was collected to determine a variant-coding sequence) and performing a sequencing analysis using the sample.

As used herein, a "variant-coding sequence" refers to a sequence that identifies amino acids within at least part of a peptide and that includes a variant that is not observed in a corresponding reference sequence. When the peptide includes a mutation or variant, the variant-coding sequence identifies amino acids of the mutation or variant. However, when the peptide does not include a mutation or variant, the variant-coding sequence does not identify amino acids of a mutation or variant (and in that instance is the same as the reference sequence). A variant-coding sequence can be determined by collecting a disease and/or tumor sample (e.g., that includes tumor cells) and performing a sequencing analysis to identify one or more sequences corresponding to disease and/or tumor cells in the sample. In some instances, a sequencing analysis outputs an amino-acid sequence. In some instances, a sequencing analysis outputs a nucleic-acid sequence, which may be subsequently processed to transform codons into amino-acid identifiers and thus to produce an amino-acid sequence. A variant-coding sequence can include a sequence of a neoantigen. A variant-coding sequence may, but need not, include one or more termini (e.g., the C-terminus and/or the N-terminus) of the peptide. A variant-coding sequence may include an epitope of the peptide. A variant-coding sequence can identify amino acids within a peptide having one or more variants (e.g., one or more amino-acid distinctions) relative to a corresponding reference sequence. In some instances, a variant-coding sequence includes an ordered set of amino acids. In some instances, a variant-coding sequence identifies a reference peptide (e.g., by identifying a genetic reference sequence, such as by gene, start position and/or end position; or by gene, start position and/or length) and one or more point mutations relative to the reference peptide.

As used herein, a "subsequence" of an MHC molecule refers to an ordered set of amino acids of the MHC molecule that makes contact with a peptide.

As used herein, a "representation" of a sequence or subsequence can include a set of values that represent or identify amino acids in the sequence or subsequence and/or a set of values that represent or identify nucleic acids that encode the sequence or subsequence. For example, a pseudo-sequence version of an MHC sequence is an exemplary embodiment of a representation of that MHC sequence. For example, each amino acid may be represented by a binary string and/or vector of values that is distinct from each other binary string and/or vector representing each other amino acid. The representation may be generated using, for example, one-hot encoding or using a BLOcks Substitution Matrix (BLOSUM) matrix. For example, a multi-dimensional (e.g., 20- or 21-dimensional) array may be initialized (e.g., randomly or pseudorandomly initialized). The initialized array may then include a unique vector corresponding to each amino acid. The values may then be fixed, such that use of any vector can be assumed to represent a corresponding amino acid. It will be appreciated that there may be multiple nucleic-acid representations of a given sequence, given that any of multiple codons encode a single amino acid.

As used herein, "presentation" of a peptide refers to at least part of the peptide being presented on a surface of a cell by being bound to an MHC molecule in a particular manner. The presented peptide can then be accessible or available to other cells, such as nearby T cells.

As used herein, a "sample" can include tissue (e.g., a biopsy), single cell, multiple cells, fragments of cells, or an aliquot of body fluid. The sample may have been taken from a subject, by means including venipuncture, excretion, ejaculation, massage, biopsy, needle aspirate, lavage sample, scraping, surgical incision, or intervention or other means known in the art.

As used herein, "binding affinity" refers to affinity of binding between a specific antigen (e.g., peptide) and an MHC molecule (and/or MHC allele). The binding affinity can characterize a stability and/or strength of the binding between the specific antigen and MHC molecule.

As used herein, "immunogenicity" refers to the ability of a foreign substance, e.g., an antigen, to elicit an immune response (e.g., via T cells, B cells, etc.) in the body of a human or another animal.

III. Training Data

An immunogenicity model can be used to generate a prediction of whether a candidate peptide is immunogenic, a likelihood that the candidate peptide is immunogenic, or a combination thereof. For example, one or more models are trained with one or more training datasets to form an immunogenicity model. This immunogenicity model can then be used to generate predictions.

A training data set can be generated using data collected from multiple samples (e.g., potentially being associated with one or more other subjects other than a subject of interest whose samples are collected to carry out an immunogenicity prediction). Each of the multiple samples can include, for example, tissue (e.g., a biopsy), single cell, multiple cells, fragments of cells or an aliquot of body fluid. In some instances, the multiple samples are collected from a different type of subject as compared to a subject associated with input data to be processed by the trained model. For example, a machine-learning model, such as a presentation model or an immunogenicity model, may be generated by training a model using training data, which are collected by processing samples from one or more cell lines or which are determined by processing one or more samples from a human subject.

The training data set can include multiple training elements. Each of the multiple training elements can include input data that includes a set of either wild-type or variant-coding sequence representations (each of which code for and/or represent any variant in a corresponding peptide) and a subsequence of an MHC molecule. The training data set can be collected in accordance with one or more techniques disclosed herein.

More than one type of training data sets or training elements (e.g., each having a different type of functional label) can be used in training an immunogenicity model as described herein. Each training element can also include one or more experiment-based results that are used as function labels (e.g., functional labels related to MHC presentation or related to immunogenicity). An experiment-based result can indicate whether to what extent each of one or more particular types of interaction between a wild-type peptide or mutant peptide (associated with a candidate peptide sequence in the training element) and an MHC molecule (associated with an MHC molecule subsequence in the training element) occurs and whether to what extent a candidate peptide sequence is immunogenic. A particular type of interaction can include, for example, binding of a peptide to an MHC molecule and/or presentation of a peptide by the MHC molecule on a surface of a cell (e.g., a tumor cell).

Moreover, an experiment-based result can include binding affinity between the peptide and the MHC molecule. The experiment-based result can include or can be based on qualitative data and/or quantitative data characterizing whether a given peptide binds with a given MHC molecule, a strength of such a bond, and/or a stability of such a bond. For example, a binary binding-affinity indicator or a qualitative binary-affinity result can be generated using an ELISA, pull-down assay, gel-shift assay, or biosensor-based methodology such as Surface Plasmon Resonance, Isothermal Titration Colorimetry, Biolayer Interferometry, or MicroScale Thermophoresis.

The experiment-based result can further or alternatively characterize whether a given MHC molecule will present a given peptide, the probability of such presentation, or both. For example, MHC ligands may be immunoprecipitated out of a sample. Subsequent elution and mass spectrometry can be used to determine whether the MHC molecule presented the ligand.

In additional and alternative embodiments, training data sets can include candidate peptide sequences with a functional label that indicates whether and/or to what extent a wild-type peptide or mutant peptide (associated with a candidate peptide sequence in the training element) is immunogenic.

The functional labels included in the training data set may indicate whether a mutant peptide with amino acids as identified by a candidate peptide sequence (e.g., a variant-coding sequence) triggered an immunogenic response in a subject other than a subject of interest or in in vitro samples of cell lines or a subject other than a subject of interest. Immunogenicity may indicate that the mutant peptide activated a T-cell receptor (e.g., a receptor of a CD8+ cytotoxic T lymphocyte or CD4+ helper T cell) and/or triggered an immunological response. The training data may have been generated by, for example, expressing various mutant peptides in a sample (e.g., one or more dendritic cells) and/or introducing various mutant peptides (e.g., to a sample or to a subject from which a sample was subsequently collected) via immunization, by a vaccine, by a personalized T-cell therapy, or a combination thereof. The mutant peptides may have been expressed or introduced individually (e.g., thereby focusing each experiment on a single mutant peptide) or in groups.

For example, immunogenicity for a functional label may have been tested by analyzing tumor infiltrating cells or other T cells. It may have been determined that a mutant peptide triggered an immunological response and/or immunogenicity if, for example, epitopes of the mutant peptide are detected (e.g., at a quantity above a threshold), a measured level of interferon gamma (IFN-γ) or T cell immunoglobulin mucin-3 (TIM-3) exceeded a corresponding threshold, a detected quantity of cytotoxic T cells (e.g., in general or cytotoxic T cells displaying an epitope corresponding to the mutant peptide) exceeded a corresponding threshold; and/or at least a threshold degree of apoptosis is observed. As another example, the mutant peptide may have been expressed in a sample (e.g., one or more dendritic cells). It may have been determined that the mutant peptide triggered an immunological response and/or immunogenicity if it is determined that the presented antigen is subsequently recognized by a T cell. It will be appreciated that some embodiments include collecting and/or determining at least part of the training data set (e.g., by performing one or more experiments and/or analyses disclosed herein).

IV. Immunogenicity Model Training Workflow

Figure 1B:
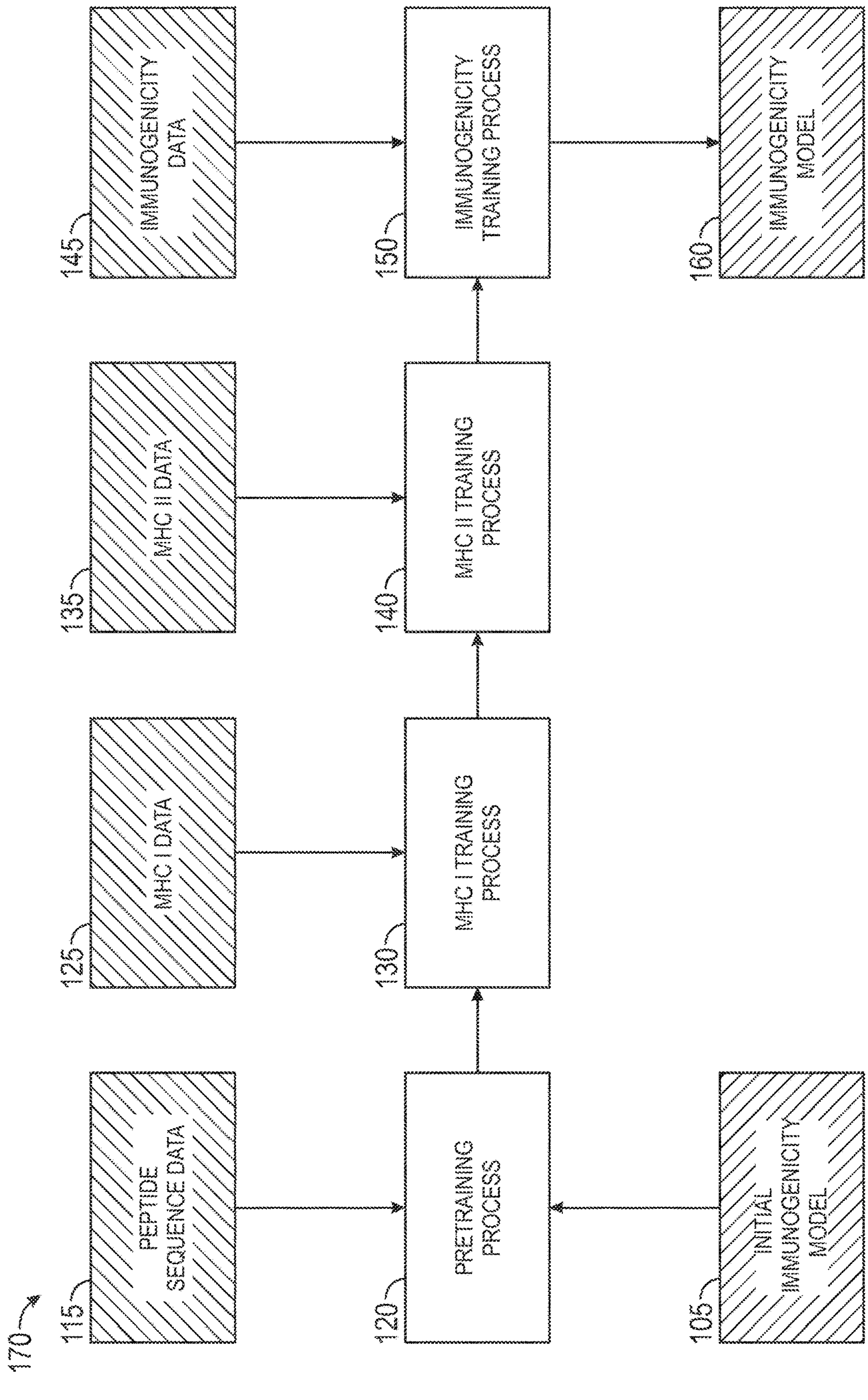
FIG. 1B is an illustration of a workflow for training an immunogenicity model to predict immunogenicity of neoantigen candidates in accordance with one or more embodiments.

Various method and system embodiments described herein enable improved prediction methods to predict immunogenicity of neoantigen candidates. FIGS. 1A-1B are schematic illustrations of two examples for a general workflow for training an immunogenicity model to predict immunogenicity of neoantigen candidates.

FIG. 1A is an illustration of a workflow 100 for training an immunogenicity model to predict immunogenicity of neoantigen candidates in accordance with one or more embodiments.

The workflow 100 shown in FIG. 1A starts with a pretrained immunogenicity model 110 and moves through subsequent training processes 130, 140, and 150 to produce an immunogenicity model 160. In other embodiments, the workflow 100 can include various combinations of features such a, for example, more or fewer features than those illustrated in FIG. 1A.

FIG. 1B is an illustration of a workflow 170 for training an immunogenicity model to predict immunogenicity of neoantigen candidates in accordance with one or more embodiments. The workflow 170 is similar to the workflow 100 in FIG. 1A but instead starts with an untrained immunogenicity model, then moves through a pretraining process 120 before moving through subsequent training processes 130, 140, and 150 to produce an immunogenicity model 160. Thus, the workflow 170 in FIG. 1B generally includes the workflow 100 in FIG. 1A and the pretraining process 120. In other embodiments, the workflow 170 can include various combinations of features such a, for example, more or fewer features than those illustrated in FIG. 1B.

A reference to data, a model, and/or a process that is included in both workflow 100 in FIG. 1A and workflow 170 in FIG. 1B may refer to the data, model, and/or process in workflow 100, in workflow 170, or both. The immunogenicity model 160 generated in FIGS. 1A and 1B may be used to predict immunogenicity of neoantigen candidates as described below with respect to workflow 200 in FIG. 2. The workflow 100 in FIG. 1A and the workflow 170 in FIG. 1B may be implemented using, for example, system 800 described with respect to FIG. 8 or a similar system.

IV.A. Obtaining a Pretrained Immunogenicity Model

As illustrated in the workflow 100 in FIG. 1A, training an immunogenicity model may include receiving or otherwise obtaining a pretrained immunogenicity model 110. The pretrained immunogenicity model 110 may be a language representation model trained on protein sequences to predict either masked amino acid(s) from a masked sequence or the next amino acid in an incomplete sequence. Using a pretrained immunogenicity model 110 can better identify latent information in peptide sequences that correlates with immunogenicity than non-language type models. In some cases, the training process for workflow 100 shown in FIG. 1A may include the various features or other aspects of the workflow 170 described in detail in section IV.B with respect to, for example, the pretraining process shown in FIG. 1B. In some embodiments, through the use of an unsupervised pretraining process, the pretrained immunogenicity model 110 gains the ability to represent the input protein sequence in a manner that can be used for downstream tasks.

The pretrained immunogenicity model 110 is then processed via subsequent training processes (e.g., training processes 130, 140, and 150) to generate an immunogenicity model 160. These subsequent training processes 130, 140, and 150 are described in detail in section IV.C.

IV.B. Pretraining

In one or more embodiments, as illustrated in the workflow 170 in FIG. 1B, training an immunogenicity model may include starting with an initial immunogenicity model 105 and then performing a pretraining process 120 to pretrain the initial immunogenicity model 105 to form a pretrained immunogenicity model such as pretrained immunogenicity model 110 in FIG. 1A. The initial immunogenicity model 105 may be, for example, an untrained immunogenicity model. For example, the initial immunogenicity model 105 can be pretrained with peptide sequence data 115 using masked-token prediction. The pretrained immunogenicity model that results from pretraining process 120 in FIG. 1B is processed via subsequent training processes (e.g., training processes 130, 140, and 150) to generate the immunogenicity model 160.

The pretraining process 120 is described in further detail in sections IV.B.1-IV.B.3. The output of the pretraining process 120 is a pretrained immunogenicity model such as the pretrained immunogenicity model 110 in FIG. 1A. As noted above, the subsequent training processes illustrated by blocks 130, 140, and 150 are described in detail in section IV.C.

IV.B.1 Input Data for the Pretraining Process

As used in the pretraining process at block 120, the peptide sequence data 115 can include any dataset of peptide sequences, including, for example, protein sequences without any functional labels. For example, the peptide sequence data 115 can include a Pfam dataset. The Pfam dataset is a subset of the UniProt database and has 31 million protein sequences or any intermediate ranges or values that belong to specific families. The peptide sequence data 115 can also be a non-Pfam dataset selected from the UniProt database, which has 300 million sequences from various sources. The portion of data used from the UniProt database may be selected to alleviate bias to certain families, to force the immunogenicity model 160 to learn from specific families (increase bias), or to change the size of the pretraining dataset.

IV.B.2 Models Used in the Pretraining Process

In one or more embodiments, the initial immunogenicity model 105 can be a neural network-based model. For example, the neural network-based model may be a transformer model, a 1D convolutional neural network model, or a recurrent neural network model. In one or more embodiments, the initial immunogenicity model 105 is a transformer-based TAPE (tasks assessing protein embeddings) model as described in Rao et al., Roshan Rao, et al. Evaluating protein transfer learning with TAPE. Adv. in Neural Information Processing Sys. (2019), which is hereby incorporated by reference in its entirety for all purposes. In some embodiments, the TAPE model can be constructed using the BERT (Bidirectional Encoder Representations from Transformers) based transformer model with semi-supervised learning as described in Devlin et al., Jacob Delvin et al., BERT: Pretraining of Deep Bidirectional Transformers for Language Understanding, arXiv (Oct. 11, 2018), https://arxiv.org/abs/1810.04805, which is hereby incorporated by reference in its entirety for all purposes.

The initial immunogenicity model 105 may include an attention-based mechanism. In some embodiments, the initial immunogenicity model 105 includes one or more transformer layers, one or more poolers, one or more fully connected layers, or a combination thereof. In some embodiments, the initial immunogenicity model 105 may use model architectures other than TAPE or BERT.

IV.B.3 Pretraining Process

During the pretraining process 120, the untrained immunogenicity model 105 is trained with peptide sequence data 115. For example, the peptide sequence data 115 may include at least or about 20, 25, 30, 31, 32, 33, 34, 35, 36, 37, 38, 39, 40, 41, 42, 43, 44, 45, 50, 55, 60, 100, 200, or 300 million protein sequences or any intermediate ranges or values. For example, the initial immunogenicity model 105 may mask at least, at most, or about 5%, 6%, 7%, 8%, 9%, 10%, 11%, 12%, 13%, 14%, 15%, 16%, 17%, 18%, 19%, or 20% of the amino acids in the peptide sequence data 115. The initial immunogenicity model 105 can be trained to predict which vocabulary token (representing a single amino acid) fits best in each masked position so that the initial parameters of an immunogenicity model can be further trained.

IV.C. Subsequent Training with Labeled Data

Subsequent training after the pretrained immunogenicity model 110 has been obtained in the workflow 100 in FIG. 1A or after the pretraining process 120 in the workflow 170 in FIG. 1B includes three training processes 130, 140, and 150. These training processes use labeled data that contains peptide sequences associated with a different functional label related to immunogenicity. For example, the MHC-I training process 130 uses MHC-I data 125 having a functional label for MHC-I binding. The MHC-II training process 140 uses MHC-II data 135 having a functional label for MHC-II binding. The immunogenicity training process 150 uses immunogenicity data 145 having a functional label for immunogenicity. At each of the subsequent training processes 130, 140, and 150, specific inputs of the labeled data (e.g., MHC-I data 125, MHC-II data 135, immunogenicity data 145) are plugged into the model resulting from the immediately preceding step to fine-tune one or more of the parameters of the model and generate the immunogenicity model 160.

IV.C.1 Labeled Data Input for the Subsequent Training Processes

In some embodiments, the labeled data, which includes, for example, MHC I data 125, MHC II data 135, and the immunogenicity data 145, may include multiple data elements, such as a candidate peptide sequence (or other representation thereof), an MHC sequence (or other representation thereof) and one or more functional labels. For example, the candidate peptide sequence can identify an ordered set of amino acids within a peptide (e.g., a neoantigen candidate). The candidate peptide sequence can identify amino acids within an epitope (e.g., that includes a variant and/or that includes or that is a neoepitope) of the peptide. The candidate peptide sequence can identify amino acids within one or more termini of a candidate peptide sequence (e.g., a C-flank corresponding to a C-terminus and/or an N-flank corresponding to an N-terminus). In some embodiments, neither the N-flank nor the C-flank bind to an MHC molecule, though each may influence whether the candidate peptide is presented by an MHC molecule.

The interaction label(s) (of a given training element) can characterize whether and/or to what extent an interaction (of a particular type) between an MHC molecule corresponding to an MHC sequence (of the given training element) and a candidate peptide corresponding to a candidate peptide sequence (of the given training element). A negative interaction label may indicate that a candidate peptide does not bind to and/or is not presented by an MHC molecule. A positive interaction label may indicate that a candidate peptide binds to and/or is presented by an MHC molecule. For example, the interaction label(s) can indicate whether the candidate peptide binds to the MHC molecule, a probability that the candidate peptide binds to the MHC molecule, binding affinity between the candidate peptide and the MHC molecule, a binding strength between the candidate peptide and the MHC molecule, a binding stability between the candidate peptide and the MHC molecule, whether the MHC molecule presents the candidate peptide (e.g., at a surface of a cell and/or at a surface of a tumor cell) and/or a probability that the MHC molecule presents the candidate peptide.

The immunogenicity label(s) (of a given training element) can characterize whether to what extent a candidate peptide corresponding to a candidate peptide sequence (of the given training element) is immunogenic based on experimental results or medical records.

The labeled training data may have been generated, for example, via in vitro or in vivo experiments and/or based on medical records. The labeled training data may have been generated based on one or more techniques disclosed in Section III.

IV.C.2 Subsequent Training Processes

With respect to the MHC I training process 130, the workflow 100 can include further training the pretrained immunogenicity model 110 or a resulting pretrained immunogenicity model from the pretraining process 120 with labeled MHC-I binding data 125. For example, the input for the MHC I training process 130 may include a set of concatenated sequences, each concatenated sequence including a candidate peptide sequence (including its N-flank regions) and its corresponding MHC-I sequence. The output of the MHC I training process 130 may be an MHC-I binding result such as classification of eluted ligand (EL) for the candidate peptide sequence, which can be a binary number (e.g., 0 indicating not binding to MHC-I or 1 indicating binding to MHC-I) or a float number.

With respect to the MHC II training process 140, the workflow 100 can include further training the pretrained immunogenicity model 110 on labeled MHC-II binding data 135. For example, the input for the MHC II training process 140 may include a set of concatenated sequences, each concatenated sequence including a candidate peptide sequence (including its N-flank regions) and its corresponding MHC-II sequence. The output of the MHC H training process 140 may be an MHC-II binding result such as a binding affinity result for the candidate peptide sequence, which can be a binary number (e.g., 0 indicating not binding to MHC-II or 1 indicating binding to MHC-II) or a float number.

With respect to the immunogenicity training process 150, the workflow 100 can include further training the pretrained immunogenicity model 110 on labeled immunogenicity data 145 to generate the immunogenicity model 160. For example, the input for the immunogenicity training process 150 may include a set of concatenated sequences, each concatenated sequence including a candidate peptide sequence (including its N-flank regions) and its corresponding MHC sequence. The output of the immunogenicity training process 150 may be an immunogenicity result for the candidate peptide sequence. The candidate peptide sequence may be selected based on an MHC presentation score meeting a pre-defined criterion, such as the most presentable neoepitope based on MHC presentation data. The most presentable neoepitope comes from neoantigens, and neoepitopes are sub-sequences of neoantigens. Different neoepitopes are scored for MHC presentation and the highest score is taken as the most presentable neoepitope. In some instances, the labeled immunogenicity data 145 may be obtained using a multimer assay, an ELISpot assay, any available immunogenicity measurement method, or a combination thereof.

At each stage of subsequent training (i.e., fine-tuning) that occurs with training processes 130, 140, and 150, the workflow 100 and/or the workflow 170 may include calculating a classification loss function, a regression loss function, or a combination thereof. For example, a loss function can be based on at least one of a mean square error, a median square error, a mean absolute error, a median absolute error, an entropy-based error, a cross entropy error, a binary cross entropy error, or another type of error or loss.

Figure 2:
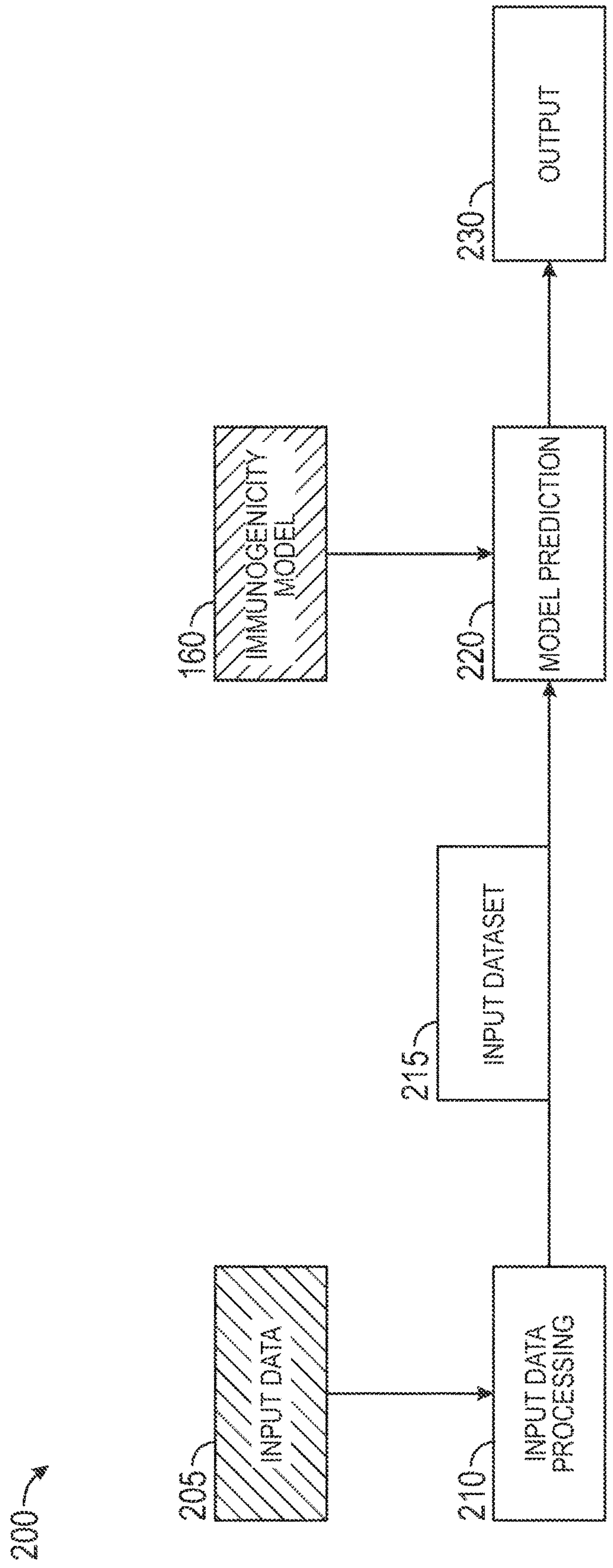
FIG. 2 is a schematic diagram of a workflow for predicting immunogenicity of neoantigen candidates in accordance with various embodiments.

In one or more embodiments, the workflow 100 and/or the workflow 170 can include using the immunogenicity model 160 for immunogenicity prediction of candidate peptide sequences such as a binary immunogenicity prediction score or a non-binary immunogenicity prediction score as further described in FIG. 2 and in section V.

After training via the training processes 130, 140, and 150, the workflow 100 and/or the workflow 170 may include using validation data (e.g., a separated subset of the training data set or a test set) to assess a performance of the immunogenicity model 160 as it is being trained or after it has been trained. The metrics of evaluation of the model's performance can include area under a receiver operating characteristic curve (i.e., ROC-AUC) and p-values as exemplified in FIG. 4 and FIG. 5, which are described in more detail in section VI. Training may be terminated if and/or when a desired performance is obtained and/or a maximum number of training iterations have been completed.

IV.C.3 Learning Rate Changes in the Subsequent Training Processes

During the MHC I training process 130, the MHC II training process 140, and the immunogenicity training process 150 in workflow 100 and/or workflow 170, the pre-trained immunogenicity model 110 is trained using a static or dynamic learning rate. For example, a dynamic learned rate can be produced using learning-rate annealing.

The pretrained immunogenicity model 110 can be a model with a plurality of layers. The training in workflow 100 and/or workflow 170 may include training different layers of the model or any of the intermediate models between the pretrained immunogenicity model 110 and the final immunogenicity model 160 with different learning rates, changing learning rates with a rising and falling phase between epochs, or a combination thereof. Discriminative learning rates are one example of learning rates that can be used during fine-tuning. For example, during fine-tuning, each transformer layer of the model may have a different learning rate. In some cases, first layers may have the lowest learning rates while the last layers having the highest learning rates. In other examples, the different layers may be grouped with a first group that includes one or more beginning layers having a lowest learning rate and a last group that includes one or more last layers having a highest learning rate.

Figure 3:
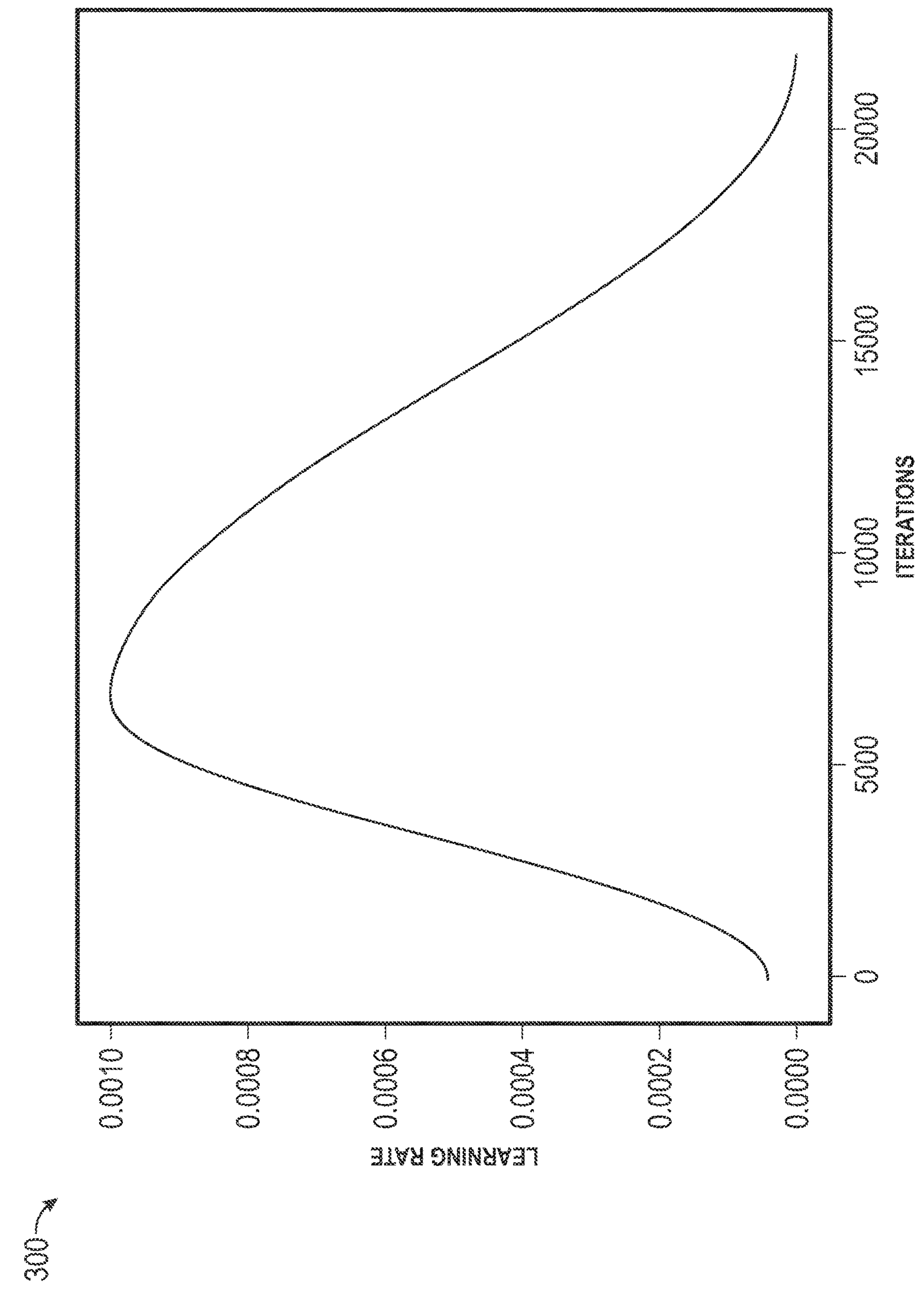
FIG. 3 is an illustration of a graph for a slanted triangular learning rate in accordance with one or more embodiments.

A slanted triangular learning rate is another example of how learning rates can be used. For example, with a slanted triangular learning rate, during fine-tuning, the learning rate changes in a triangular pattern, first increasing then decreasing (or decaying). In some examples, the learning rate changes in a non-linear manner, such as a cosine annealing change of learning rate at both the rising and the falling sections of the triangle (as illustrated in FIG. 3). This slanted triangular learning rate may allow a more stable training process and improved final performance.

FIG. 3 is an illustration of a graph for a slanted triangular learning rate in accordance with one or more embodiments. In FIG. 3, graph 300 depicts the change in learning rate that occurs during subsequent training of an immunogenicity model for predicting immunogenicity of candidate peptide sequences (e.g., the training performed to generate immunogenicity model 160 in FIGS. 1A and 1B). The graph 300 shows how the learning rate (Y axis) for the last layer of an immunogenicity model changes during training iterations (i.e., training batches through time) (X axis). The graph 300 shows a cosine annealing change of learning rate at both the rising and the falling sections of the triangle. This non-linear change in learning rates during training improves fine-tuning and ensures a more stable training process. This type of learning rate scheduling may occur every time fine-tuning occurs, first when the last two layers are unfrozen, and again when everything is unfrozen.

IV.C.4 Unfreezing in the Subsequent Training Processes

In one or more embodiments, each of the training (i.e., fine-tuning) processes 130, 140, and 150 in workflow 100 and/or workflow 170 may include a warm-up period during which the training (i.e., fine-tuning) starts from the last layer one or two lawyers. For example, the last two transformer layers may be first fine-tuned during a first period, followed by a second period during which all of the transformer layers of the model are fine-tuned. In some examples, learning rate scheduling occurs every time fine-tuning occurs, first when the last two layers are unfrozen, and again when everything is unfrozen.

For example, the workflow 100 and/or the workflow 170 may include unfreezing the last two transformer layers, the pooler, and the fully connected layer (e.g., the total last 4 layers of the network). Then, after a warmup period, the rest of the network is unfrozen. Since the last layers are the ones that move the most even with normal fine-tuning, have classification capacity, and are trained for language modeling during fine-tuning for down-stream tasks, it can be desirable to move or tune one or more of the last layers first and avoid moving or tuning the inner general layers.

V. Immunogenicity Prediction Workflow

FIG. 2 is a schematic diagram of a workflow 200 for predicting immunogenicity of neoantigen candidates in accordance with various embodiments. This workflow 200 allows for selection of candidate peptides with desired immunogenicity for use in a personalized therapy. FIG. 2 illustrates one example of an implementation for a workflow for predicting immunogenicity of neoantigen candidates. In other embodiments, the workflow 200 may include one or more features or various combinations of features, whether it be more or fewer features than those illustrated in FIG. 2. The workflow 200 may be implemented using, for example, system 800 described with respect to FIG. 8 or a similar system.

V.A. Input Data

The workflow 200 includes collecting, obtaining, retrieving, and/or accessing input data 205, which includes input sequences of candidate peptide sequences that can be used to identify candidate neoantigens, or particularly candidate neoepitopes with desired immunogenicity.

Generally, the candidate peptide sequences are associated with a diseased sample, such as one or more samples from one or more diseases patients, e.g., patients that have one or more tumors. The candidate peptide sequences may have been obtained by identifying peptide sequences within a diseased sample of the subject and determining which of the peptide sequences are not represented within a reference sample, healthy-sample, and/or wild-type sequence set. When a healthy sample is used for the comparison, the healthy sample may have been (but need not have been) collected from the subject.

The candidate peptide sequences can include a subject-specific set of candidate peptide sequences. The subject-specific set of candidate peptide sequences can correspond to a set of mutant peptides, such that each of the subject-specific set of candidate peptide sequences correspond to amino acids within a mutant peptide of the set of mutant peptides and/or such that each of the subject-specific set of candidate peptide sequences correspond to one or more amino acids in a mutation. Each of the subject-specific set of candidate peptide sequences can be associated with a particular subject (e.g., human subject). The particular subject may have been diagnosed with, may have and/or may have experienced symptoms or test results associated with a particular medical condition (e.g., cancer).

The candidate peptides sequences may have been identified by processing a diseased sample from a tumor. A tumor can include one or more of lung cancer, melanoma, breast cancer, ovarian cancer, prostate cancer kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, T-cell prolymphocytic leukemia (T-PLL), non-small cell lung cancer, small-cell lung cancer, or any other cancer type.

Each candidate peptide sequence of the input data may be associated with a major histocompatibility complex (MHC) presentation score meeting a pre-set criterion, wherein each MHC presentation score indicates a level of likelihood that each candidate peptide sequence is determined to be presented by a corresponding MHC peptide sequence.

The MHC presentation score can be predicted using a neural network-based model, such as an attention-based model. Having a pre-selection of candidate peptide sequences based on an MHC presentation score can improve accuracy of immunogenicity prediction and facilitate selection of peptides with a desired MHC presentation property and immunogenicity for therapeutic development.

The input data 205 of the workflow 200 can include not only the peptide sequence themselves, but also adjacent portions of the candidate peptide sequence such as a sequence at an N-flank and/or C-flank region of an epitope of the candidate peptide sequence.

The workflow 200 can include retrieving or accessing input data 205 from a local or remote storage and/or requesting input data of candidate peptide sequences from another device. Retrieving or accessing the input data of candidate peptide sequences can include and/or can be performed in combination with determining the candidate peptide sequences for input data collection.

The input data 205 of the candidate peptide sequences may have been identified using a technique disclosed herein or any available technique. The set of candidate peptide sequences can include one, two, three, or more peptide sequences. A candidate peptide sequence can include a variant coding sequence corresponding to a mutant peptide and one or more other sequences or subsequences (e.g., corresponding to an MHC-I molecule, an MHC-II molecule, or a T-cell receptor).

In some instances, predictions are generated for one or more of a set of candidate peptide sequences (corresponding to a set of mutant peptides). The set of candidate peptide sequences can correspond to peptides present in a diseased sample collected from the subject but that are not observed in one or more non-diseased samples (e.g., from the subject or another subject). For example, the candidate peptide sequences may have been identified by performing a peptide or nucleic-acid sequencing technique to identify peptide sequences or nucleic acid sequences in a diseased sample and comparing the identified peptides to those detected in a healthy sample or reference database to identify tumor-specific peptide or nucleic-acid sequences. If the tumor-specific sequences are nucleic-acid sequences, each tumor-specific nucleic-acid sequence may be converted into an amino-acid sequence.

A variety of methods are available for identifying a set of mutant peptides associated with a given subject. Mutations can be present in the genome, transcription, proteome or exome of diseased cells of a subject but absent in a non-diseased sample (e.g., a non-diseased sample from the subject or from another subject). Mutations include, but are not limited to, (1) non-synonymous mutations leading to different amino acids in the protein; (2) read-through mutations in which a stop codon is modified or deleted, leading to translation of a longer protein with a novel tumor-specific sequence at the C-terminus; (3) splice site mutations that lead to the inclusion of an intron in the mature mRNA and thus a unique tumor-specific protein sequence; (4) chromosomal rearrangements that give rise to a chimeric protein with tumor-specific sequences at the junction of 2 proteins (i.e., gene fusion); (5) frameshift insertions or deletions that lead to a new open reading frame with a novel tumor-specific protein sequence. Mutations can also include one or more of nonframeshift indel, missense or nonsense substitution, splice site alteration, genomic rearrangement or gene fusion, or any genomic or expression alteration giving rise to a neoORF.

Peptides with mutations or mutated polypeptides arising from, for example, splice-site, frameshift, readthrough, or gene fusion mutations in diseased cells can be identified by sequencing DNA, RNA or protein in the diseased sample and comparing the obtained sequences with sequences from a non-diseased sample.

In some embodiments, whole genome sequencing (WGS) or whole exome sequencing (WES) data from a diseased sample and a non-diseased sample can be obtained and compared. Following the alignment of non-diseased sample and diseased sample reads to the human reference genome, somatic variants, which include single nucleotide variants (SNV), gene fusions and insertion or deletion variants (indels), can be detected using variant-calling algorithms. One or more variant callers can be used to detect different somatic variant types (i.e., SNV, gene fusions, or indels), for example, as shown in Xu, Chang Xu, A review of somatic single nucleotide variant calling algorithms for next-generation sequencing data, 16 Comput. Struct. Biotechnol. J., 15-24 (2018), which is hereby incorporated by reference in its entirety for all purposes.

In some examples, the mutant peptides are identified based on the transcriptome sequences in the diseased sample from the individual. For example, whole or partial transcriptome sequences (e.g., obtained via RNA-Seq) can be obtained from a diseased tissue of the individual and subjected to sequencing analysis. The sequences obtained from the diseased tissue sample can then be compared to those obtained from a reference sample. Optionally, the diseased tissue sample is subjected to whole-transcriptome RNA-Seq. Optionally, the transcriptome sequences are "enriched" for specific sequences prior to the comparison to a reference sample. For example, specific probes can be designed to enrich certain desired sequences (for example disease-specific sequences) before being subjected to sequencing analysis. Methods of whole-transcriptome sequencing and targeted sequencing are known in the art and reported in various articles including: Fuchau Tang et al., mRNA-Seq whole-transcriptome analysis of a single cell, 6 Nature Methods, 377-382 (2009); Fatih Ozsolak, et al., RNA sequencing: advances, challenges and opportunities, 12 Nature Reviews, 87-98 (2011); Marcelo A. German et al., Global identification of microRNA-target RNA pairs by parallel analysis of RNA ends, 26 Nature Biotechnology, 941-946 (2008); and Zhong Wang et al., RNA-Seq: a revolutionary tool for transcriptomics, 10 Nature Reviews, 57-63 (2009). Each of these references is hereby incorporated by reference in its entirety for all purposes.

In some embodiments, transcriptomic sequencing techniques include, but are not limited to, RNA poly(A) libraries, microarray analysis, parallel sequencing, massively parallel sequencing, PCR, and RNA-Seq. RNA-Seq is a high-throughput technique for sequencing part or substantially all of the transcriptome. In short, an isolated population of transcriptomic sequences is converted to a library of cDNA fragments with adaptors attached to one or both ends. With or without amplification, each cDNA molecule is then analyzed to obtain short stretches of sequence information, typically 30-400 base pairs. These fragments of sequence information are then aligned to a reference genome, reference transcripts, or assembled de novo to reveal the structure of transcripts (i.e., transcription boundaries) and/or the level of expression.

Once obtained, the sequences in the diseased sample can be compared to the corresponding sequences in a reference sample. The sequence comparison can be conducted at the nucleic acid level, by aligning the nucleic acid sequences in the disease tissue with the corresponding sequences in a reference sample. Genetic sequence variations that lead to one or more changes in the encoded amino acids are then identified.

Alternatively, the sequence comparison can be conducted at the amino acid level, that is, the nucleic acid sequences are first converted into amino acid sequences in silico before the comparison is carried out. Either the amino-acid-based approach or the nucleic-acid-based approach can be used to identify one or more mutations (e.g., one or more point mutations) in the peptide. With regard to nucleic-acid-based approaches, the discovered variants can be used to identify one or more nucleic-acid sequences (e.g., DNA sequences, RNA sequences or mRNA sequences) that would give rise to a given observable mutant protein (e.g., via a look-up table that associated individual peptide mutations with multiple codon variants).

In some embodiments, comparison of a sequence from the diseased sample to those of a reference sample can be completed by techniques known in the art, such as manual alignment, FAST-All (FASTA), and Basic Local Alignment Search Tool (BLAST). In some embodiments, comparison of a sequence from a diseased sample to those of a reference sample can be completed using a short-read aligner, for example GSNAP, BWA, and STAR.

In some embodiments, the reference sample is a matched, disease-free sample. As used herein, a "matched," disease-free tissue sample is one that is selected from the same or similar sample, for example, a sample from the same or similar tissue type as the diseased sample. In some embodiments, a matched, disease-free tissue and a disease tissue may originate from the same subject. The reference sample described herein in some embodiments is a disease-free sample from the same subject. In some embodiments, the reference sample is a disease-free sample from a different subject (e.g., a subject not having the disease). In some embodiments, the reference sample is obtained from a population of different subject. In some embodiments, the reference sample is a database of known genes associated with an organism. In some embodiments, a reference sample may be from a cell line. In some embodiments, a reference sample may be a combination of known genes associated with an organism and genomic information from a matched disease-free sample. In some embodiments, a variant-coding sequence may comprise a point mutation in the amino acid sequence. In some embodiments, the variant-coding sequence may comprise an amino acid deletion or insertion.

In some embodiments, the set of variant-coding sequences are first identified based on genomic and/or nucleic-acid sequences. This initial set is then further filtered to obtain a narrower set of expression variant-coding sequences based on the presence of the variant-coding sequences in a transcriptome sequencing database (and is thus deemed "expressed"). In some embodiments, the set of variant-coding sequences are reduced by, for example, at least about 10, 20, 30, 40, 50, or some other number of times by filtering through a transcriptome sequencing database.

Alternatively, any peptide sequencing methods such as protein mass spectrometry can be used to identify or validate the presence of mutant peptides from diseased samples such as tumor cells. Peptides can be acid-eluted from diseased cells (e.g., tumor cells) or from HLA molecules that are immunoprecipitated from the tumor, and then identified using mass spectrometry.

A mutant peptide can have, for example, 5 or more, 8 or more, 11 or more, 15 or more, 20 or more, 40 or more, 80 or more, 100 or more, 110 or fewer, 100 or fewer, 80 or fewer, 60 or fewer, 50 or fewer, 40 or fewer, 30 or fewer, 25 or fewer, 20 or fewer, 18 or fewer, 15 or fewer or 13 or fewer amino acids.

MHC-I sequences and/or MHC H sequences can be determined, for example, via HLA genotyping or mass spectroscopy as described in Etienne Caron et al., Analysis of Major Histocompatibility Complex (MHC) Immunopeptides Using Mass Spectroscopy, 14(12) Molecular and Cellular Proteomics, 3105-3117 (2015), which is hereby incorporated by reference in its entirety for all purposes.

V.B. Input Data Processing

The workflow 200 includes input data processing 210 to generate an input dataset 215 based on the candidate peptide sequences. The input dataset 215 is used as an input for an immunogenicity model to generate a prediction of immunogenicity for the candidate peptide sequences. For example, the input dataset 215 for prediction can include at least two sequences, such as a combination of a representation of candidate peptide sequences and a representation of MHC sequences. The combined representation may include a concatenated sequence of a candidate neoepitope (e.g., a candidate peptide sequence, including its N-terminal flank region) and an MHC sequence.

The input data processing 210 may include identifying a corresponding MHC sequence for each candidate peptide sequence. Both the candidate peptide sequence and the corresponding MHC sequence can be processed to generate a combination of the candidate peptide sequence and the corresponding MHC sequence as input data.

In some instances, the input data processing 210 includes identifying the MHC sequence and the candidate peptide sequences using a same sample (e.g., from the same subject). In some instances, the input data processing 210 includes identifying the MHC sequence and the candidate peptide sequences using multiple samples (e.g., from the same subject and/or from the subject and a different subject). In some instances, the input data processing 210 includes determining the MHC sequence using, for example, a sequencing and/or mass-spectrometry technique.

The MHC sequence can include amino acids within part or all of an MHC molecule (e.g., an MHC-I molecule or an MHC-II molecule) or a pseudo-sequence of an MHC molecule. The MHC sequence can include a subsequence of the MHC molecule, corresponding to a portion of a full MHC sequence, and the portion coding a part of the MHC molecule configured to bind to and/or present peptides. The subsequence can include a sequence corresponding to the binding pocket where the MHC molecule contacts the peptide. For example, the MHC sequence can include an MHC subsequence (e.g., which may include, for example, 34 amino acids). The MHC sequence can identify amino acids encoded by nucleic acid sequences within, for example, 1, 2, 3, 4, 5 or 6 HLA alleles. The MHC sequence can identify amino acids encoded by part or all of an HLA molecule.

V.C. Immunogenicity Model

The workflow 200 includes obtaining an immunogenicity model 160 trained with one or more training datasets as described in FIGS. 1A-1B. The one or more training datasets can include peptide sequence data 115 for initial training (i.e., pretraining) of a model and labeled data (e.g., MHC I data 125, MHC II data 135, and immunogenicity data 145) for subsequent training (e.g., fine-tuning) of the model.

V.D. Using the Immunogenicity Model for Prediction

The workflow 200 can include model prediction 220, a step that uses the immunogenicity model 160 to generate an output 230 based on a prediction result for candidate peptide sequences in the input dataset 215. The result may be a real number, an integer, categorical and/or binary. For example, a result may correspond to a prediction as to whether or not a mutant peptide represented by the candidate peptide sequences triggers an immunological response In some instances, the set of candidate peptide sequences is filtered, ranked and/or otherwise processed based on the results. For example, the set may be filtered to exclude sequences for which a predicted immunogenicity was below a pre-defined immunogenicity threshold. In some instances, a filtering is performed to identify a predetermined number and/or fraction of the candidate peptide sequences. For example, a filtering can be performed to identify, for example, 10, 20, 40, 60, 80, 100, 500, 1,000, or another number of candidate peptide sequences associated with relatively high predicted probabilities (e.g., relative to unselected candidate peptide sequences in the set) as to whether the mutant peptide will be immunogenic.

The output 230 may identify one or more candidate peptide sequences (e.g., that were not filtered out from the set) and/or one or more mutant peptides (e.g., associated with selected candidate peptide sequences). Each mutant peptide may be identified, for example, by its name, by its sequence and/or by identifying both a corresponding wild-type sequence and a variant represented in a variant-coding sequence.

The output may, but need not, identify one or more predicted results associated with each candidate peptide sequence or mutant peptide. The output may, for example, be presented locally (e.g., at a user device) and/or transmitted to another device (e.g., a cloud computing system and/or a user device associated with a medical profession or laboratory professional).

VI. Example Immunogenicity Model and Results

Figure 4:
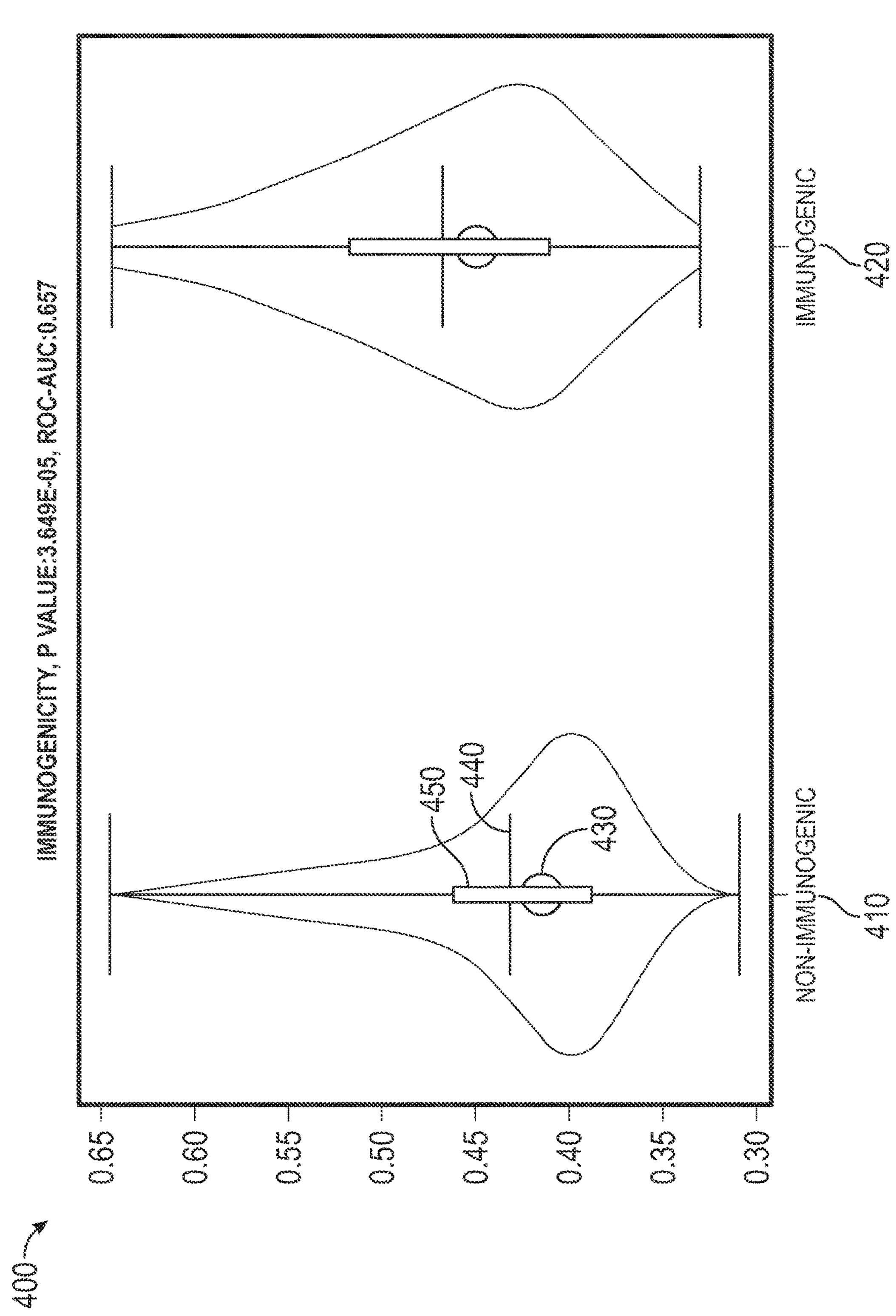
FIG. 4 is a graph demonstrating the performance of using an immunogenicity model for immunogenicity prediction in accordance with various embodiments.

To demonstrate that an example immunogenicity model, such as a TAPE model developed and trained according to the processes described with respect to in FIGS. 1A-1B, can be used to predict immunogenicity according to the processes described with respect to FIG. 2, the TAPE model's performance was evaluated (as shown in FIG., 4) and was compared with other models (as shown in FIG. 5). Example approaches for training and evaluating the performance of an example immunogenicity model, as shown in FIG. 4 and FIG. 5, are described below in section VI.A. Other methods for measuring immunogenicity that are available in the art can also be used. The descriptions of FIG. 4 and FIG. 5 are provided in section VI. B.

VI.A. Immunogenicity Dataset for Training and Prediction of an Immunogenicity Model Training via the immunogenicity training process 150 in FIGS. 1A-1B and evaluating the performance of the immunogenicity model 160 resulting from the immunogenicity training process 150 included using an immunogenicity dataset (e.g., one example of an implementation for immunogenicity data 145 in FIGS. 1A-1B). The immunogenicity dataset included data from oncology subjects who had their DNA sequenced. The subjects were subsequently dosed with an RNA vaccine. T cell responses to the neoantigens introduced in the RNA vaccine were monitored in the dosed subjects using multimer and ELISPOT assays. T cell responses believed to be technical artifacts were removed.

VI.A.1 Dosed Subject Multimer Assay

Multimer assay data was assessed for a positive or negative outcome with respect to detection of a CD8 T cell by peptide-MHC multimers. Conservative criteria was used to declare a positive outcome. Specifically, a positive outcome was declared for dual tetramer positive CD8 T cell count greater than 0.05%. In some cases, some neoepitopes were declared positive despite having lower than 0.05% neoepitope-specific CD8 T cells, if closer examination of the T cell phenotype strongly suggested a T cell response. From the multimer assay data, 1318 neoepitopes were declared negative, and based on the conservative criteria, a small fraction of these were expected to be false negatives. Further, 27 neoepitope-HLA pairs were declared as positive only post-vaccination (referred to as de novo responses) and 20 pairs were declared as pre-existing CD8 T cell responses.

VI.A.2. Dosed Subject ELISpot Assay

ELISpot data was collected and a statistical assessment of the data was conducted. Spot counts of negative controls without peptide restimulation and test cases with peptide restimulations were assessed to declare positive calls (using a permutations approach). These positive calls were verified manually. A positive or negative outcome was assigned for the immunogenicity of a given neoantigen for a given subject visit. A neoantigen was declared as positive in the ELISpot assay if it showed a positive outcome in any of the subject visits, whether pre-treatment or post-treatment. Neoantigens were further filtered based on the following criteria: (1) adjudicator-decided assay outcome value not being 'NA'; (2) none of one or more MHC presentation and/or binding affinity prediction methods (e.g., IEDBv2.13, NetMHCpan-4.0) having assigned an 'NA' value to the neoantigen; and (3) removal of pooled neoantigens used for restimulation from consideration.

After filtering as described above, the distribution of positive (immunogenic) and negative (non-immunogenic) neoantigens for each cell type evaluated in the ELISpot assays was evaluated. Immunogenic neoantigens were labeled as assay.value_binary=TRUE; non-immunogenic neoantigens were labeled as assay.value_binary=FALSE.

The positive assays were further classified into two sets, based on spot counts from the ELISpot assay. Each ELISpot assay had replicate experiments, and a mean spot count was specified across the replicates. For a positive neoantigen, the maximum value of the mean spot count across all visits was considered to split the positive neoantigens into two sets: one set for positive neoantigens with the maximum mean spot count of <50, and the other set with the maximum mean spot count of >=50. The latter set represents neoantigens that induced more extensive T cell responses and is less likely to contain false positive interpretations of the ELISpot results compared to the set with fewer spot counts. The choice of 50 spots was an arbitrary decision, as it was reasonably higher than the original threshold used for calling ELISpot positives (spot count >15).

VI.B. Evaluating the Prediction of an Immunogenicity Model

FIG. 4 is a graph 400 demonstrating the performance of using an immunogenicity model for immunogenicity prediction in accordance with various embodiments. The graph 400 shows a validation of how the immunogenicity model performs on an immunogenicity dataset using a 5-fold cross validation technique. The depicted immunogenicity model was a TAPE model that was pretrained with unlabeled protein sequences and that was subsequently trained with labelled MHC I and MHC II binding data and immunogenicity data according to the processes described with respect to FIGS. 1A-1B. The TAPE model was used on an immunogenicity dataset for validation of its performance on prediction of the immunogenicity of the immunogenicity dataset.

The immunogenicity dataset for validation includes a subset of non-immunogenic data points and a subset of immunogenic data points that can be compared to evaluate the immunogenicity model's performance. Violin plots are used to show the performance of the immunogenicity model. In a violin plot illustrated in FIG. 4, the central dot 430 is the median of prediction scores for predicting immunogenicity of the non-immunogenic data 410 and immunogenic data 420; the line 450 represents the quartile boundaries of the prediction scores; and the line 440 is the mean of the prediction scores.

In evaluating the performance of predicting immunogenicity, the null hypothesis of the experiment is that the predictions scores (Y axis) made by the immunogenicity model for non-immunogenic data 410 and immunogenic data 420 (X axis) are from the same distribution (and that the model has not learned the difference). By showing an opposite of the null hypothesis, the violin plots in FIG. 4 demonstrate how the immunogenicity model's output distribution (i.e., the distribution of the prediction scores along the Y axis) is different between the immunogenic data 420 and the non-immunogenic data 410, which in turn, demonstrates the discriminative capabilities of the immunogenicity model to predict immunogenicity.

FIG. 5 is a table 500 comparing different models for immunogenicity prediction, including the immunogenicity model used in FIG. 4 in accordance with various embodiments. The baseline model (510) and the TAPE models (520, 530, and 540) in FIG. 5 were pretrained on peptide sequence data as exemplified in FIGS. 1A-1B but were built using different subsequent training methods.

The baseline model 510 ("Zero-Shot MHC I") is a TAPE model that was pretrained on unlabeled data and subsequently trained on MHC I data (but not trained on immunogenicity data). The "TAPE+ immunogenicity" model 520 represents a TAPE model that was pretrained on unlabeled data and subsequently trained on the immunogenicity data. The "TAPE+MHC I+ immunogenicity" model 530 shows a TAPE model that was pretrained on unlabeled data and subsequently trained on MHC I data and the immunogenicity data. The "TAPE+MHC I+MHC II+ immunogenicity" model 540 shows a TAPE model that was pretrained on unlabeled data and subsequently trained on MHC I, MHC II, and the immunogenicity data. The "TAPE+MHC I+MHC II+ immunogenicity" model 540 is the TAPE model that was used to generate the results depicted in FIG. 4. As shown in the table 500, the "TAPE+MHC I+MHC II+ immunogenicity" model 540 showed at least a comparable performance with the baseline model 510 and better performance than the "TAPE+ immunogenicity" model 520 and the "TAPE+MHC I+ immunogenicity" model 530.

Therefore, FIG. 5 demonstrates that the "TAPE+MHC I+MHC II+ immunogenicity" model 540 is the most stable training method for predicting immunogenicity among the three TAPE models 520, 530, and 540.

VII. Immunogenicity Predicting Methods

Various method and system embodiments described herein enable improved prediction methods to predict immunogenicity of neoantigen candidates. In particular, the embodiments described herein enable identifying neoantigen candidates with a desired immunogenicity.

Methods are provided for predicting immunogenicity of neoantigen candidates. The methods (e.g., the method in FIG. 6) may incorporate one or more features of the workflow 100 in FIG. 1A, workflow 170 in FIG. 1B, or workflow 200 in FIG. 2. The methods can be implemented via computer software or hardware, or a combination thereof, for example, as exemplified in FIG. 8. The methods can also be implemented on a computing device/system that can include a combination of engines for predicting immunogenicity of neoantigen candidates. In various embodiments, the computing device/system can be communicatively connected to one or more of a data source, a data analyzer, and a display device via a direct connection or through an internet connection.

Figure 6:
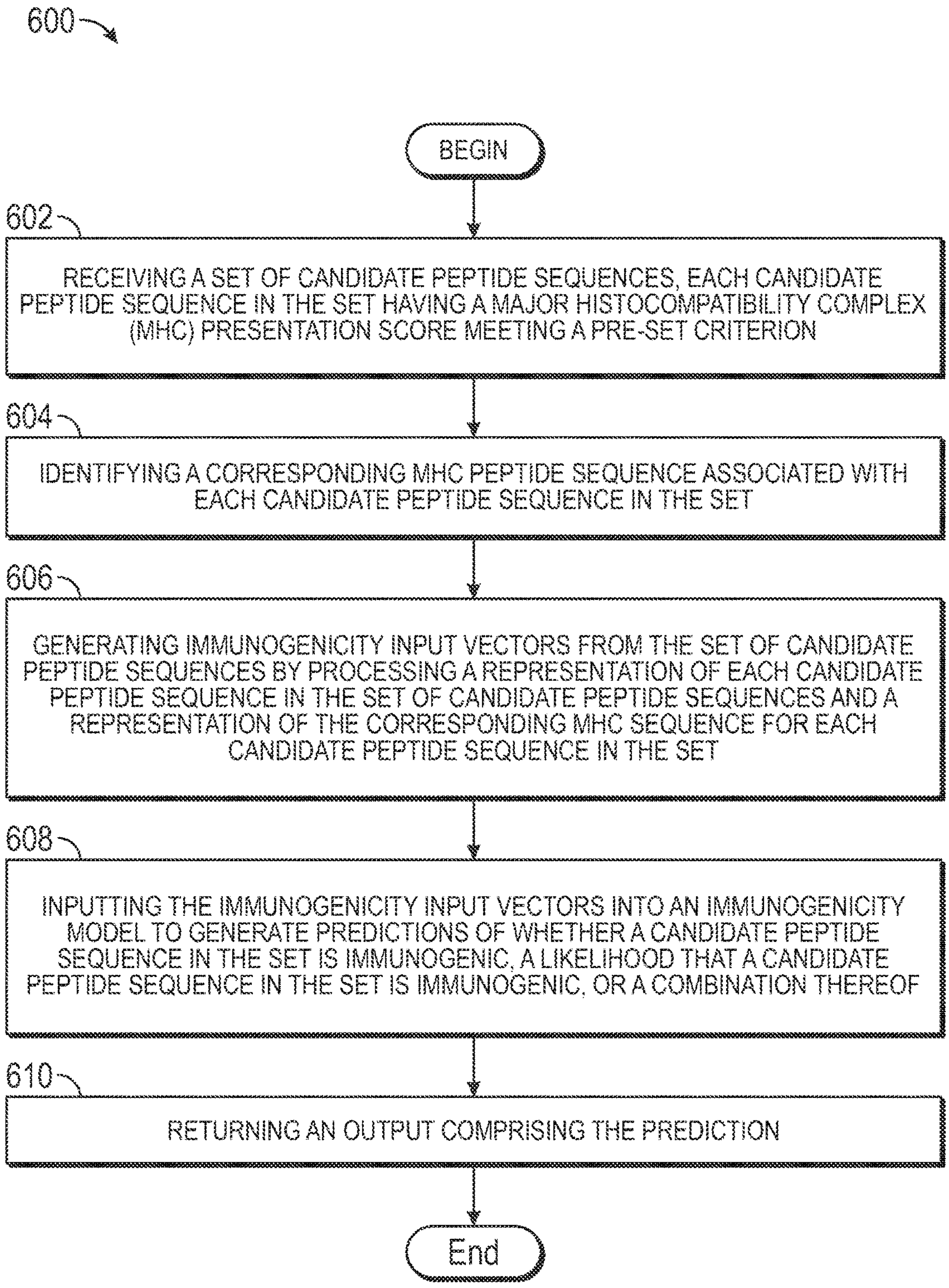
FIG. 6 is a flowchart of a method for predicting immunogenicity of candidate peptide sequences, in accordance with various embodiments.

Referring now to FIG. 6, a flowchart illustrating an example method 600 for predicting immunogenicity of candidate peptide sequences is disclosed, in accordance with various embodiments. The method 600 includes, at step 602, receiving a set of candidate peptide sequences. Each candidate peptide sequence in the set has a major histocompatibility complex (MHC) presentation score meeting a pre-set criterion, such as a pre-defined threshold or a top-ranked number. The set of candidate peptide sequences is associated with a diseased sample of a subject. The MHC presentation score indicates a likelihood that a corresponding candidate peptide sequence in the set is presented by an MHC protein on a cell surface of the diseased sample.

In various embodiments, the step 602 further includes determining an MHC presentation score for each candidate peptide sequence of the set. The MHC presentation score can be determined by receiving an initial set of candidate peptide sequences, wherein each candidate peptide sequence of the initial set is associated with the diseased sample; identifying a corresponding MHC peptide sequence for each candidate peptide sequence of the initial set; generating a presentation input vector by processing, for each of the initial set of candidate peptide sequences, a representation of each candidate peptide sequence in the initial set and a representation of the corresponding MHC peptide sequence for each candidate peptide sequence in the initial set; inputting the presentation input vector into a presentation model to determine an MHC presentation score for each candidate peptide sequence in the initial set; and selecting the set of candidate peptide sequences from the initial set of candidate peptide sequences based on the MHC presentation score.

The method 600 includes, at step 604, identifying a corresponding MHC peptide sequence associated with each candidate peptide sequence in the set. For example, the corresponding MHC peptide sequence for a candidate peptide sequence of the set comprises an abbreviated pseudo-sequence of the corresponding MHC peptide sequence of the subject. For example, the corresponding MHC peptide sequence associated with each candidate peptide sequence in the set is an MHC-I peptide sequence or an MHC-II peptide sequence.

For example, each candidate peptide sequence of the set comprises a N-terminus sequence of a candidate peptide sequence and an epitope of the candidate peptide sequence. In some instances, one or more of the candidate peptide sequences of the set have one or more mutations compared to a corresponding reference sequence associated a healthy sample of the subject. For example, the set of the candidate peptide sequences is associated with a diseased sample such as a tumor sample or a sample from a subject that has been determined to have a tumor.

The method 600 includes, at step 606, generating immunogenicity input vectors from the set of candidate peptide sequences by processing a representation of each candidate peptide sequence in the set of candidate peptide sequences and a representation of the corresponding MHC sequence for each candidate peptide sequence in the set.

The method 600 includes, at step 608, inputting the immunogenicity input vectors into an immunogenicity model to generate predictions of whether a candidate peptide sequence in the set is immunogenic, a likelihood that a candidate peptide sequence in the set is immunogenic, or a combination thereof. For example, the immunogenicity model is a neural network-based model, such as a transformer-based model having a plurality of layers.

In one or more embodiments, the immunogenicity model was initially trained (pretrained) with unlabeled peptide sequences from a protein database. The immunogenicity model was then subsequently trained with an MHC-I binding dataset comprising peptide sequences labeled with MHC-I binding, an MHC-II binding dataset comprising peptide sequences labeled with MHC-II binding, an immunogenicity dataset comprising peptide sequences labeled with immunogenicity, or a combination thereof. Training may have included unfreezing different ones of the layers of the immunogenicity model in different epochs, training different ones of the layers with different learning rates, changing learning rates with a rising and falling phase between epochs, or any combination thereof. For example, training of the immunogenicity model may have included unfreezing the last two layers of the immunogenicity model followed by unfreezing other layers of the immunogenicity model. In some cases, the immunogenicity model was trained by changing learning rates with a non-linear rising and falling phase.

The method 600 includes, at step 610, returning an output comprising the prediction. For example, the step 610 may include generating predictions for a set comprising a plurality of candidate peptide sequences, generating a report that ranks the plurality of candidate peptide sequences based on their predicted likelihood of being immunogenic, or both.

In one or more embodiments, the method 600 can further include preparing a vaccine composition comprising a candidate peptide sequence that is selected from the set based on the prediction indicating that the candidate peptide sequence is immunogenic, providing a treatment recommendation to the subject, wherein the treatment recommendation comprises administering the vaccine composition to the subject, or both.

The method 600 can further include selecting an immunogenic peptide from the set based on the prediction and preparing a therapeutic composition comprising a therapeutic agent that targets or comprises the immunogenic peptide. The method 600 can further include providing a treatment recommendation to the subject, wherein the treatment recommendation comprises administering the therapeutic composition to the subject.

Figure 7:
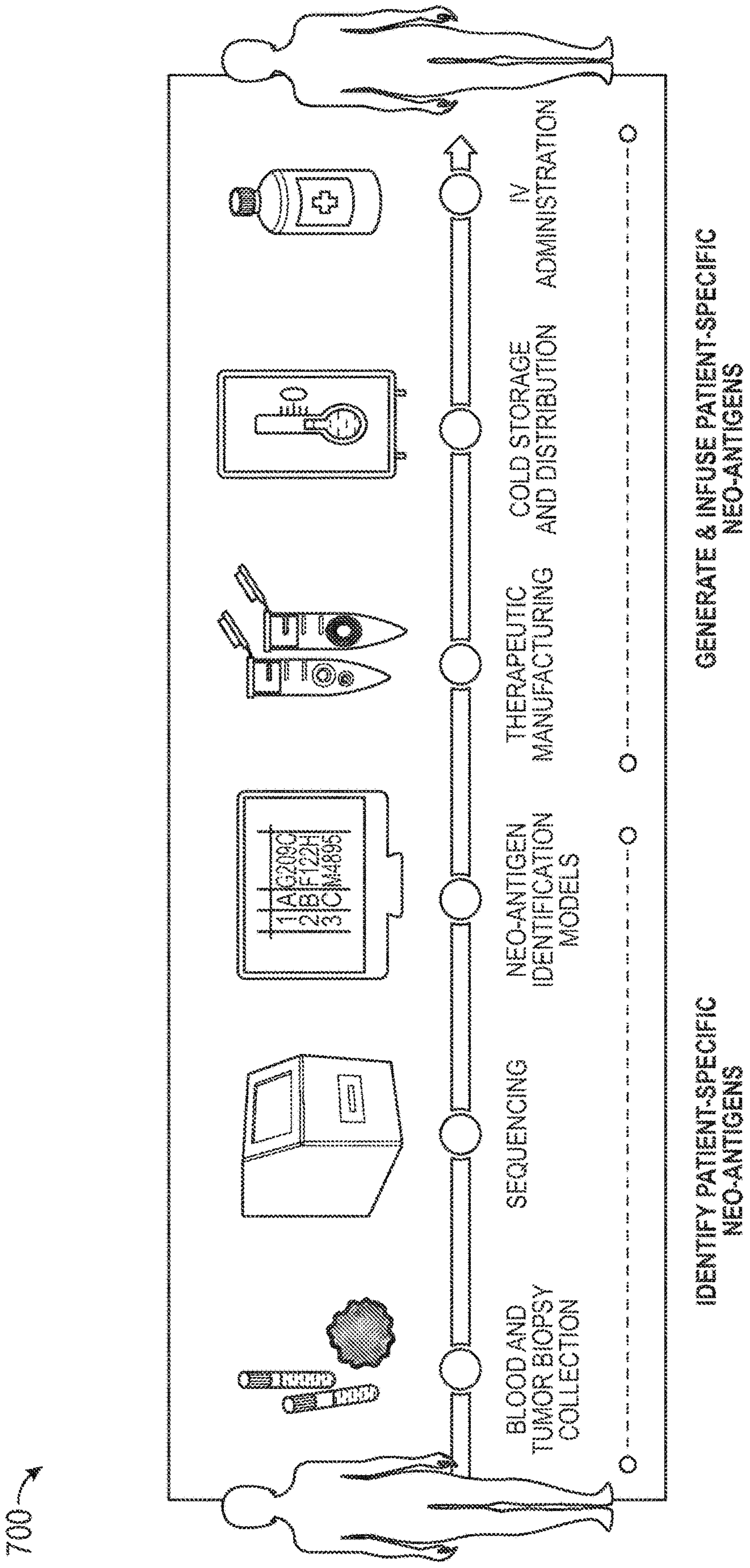
FIG. 7 is a flowchart of a method for manufacturing vaccines and therapeutics, in accordance with various embodiments.

VIII. Pharmaceutically Acceptable Composition and Manufacture Including Immunogenic Vaccines or T Cells Methods and systems described herein can be used to develop pharmaceutically acceptable compositions and manufacture therapeutic agents, for example, for personalized therapy. As illustrated in FIG. 7, a method 700 shows exemplary embodiments of a process n which patient-specific neoantigens can be identified and can be used to manufacture patient-specific neoantigen-based vaccines and therapeutic agents, such as T-cell therapies. For example, one or more patient-specific samples can be collected from a particular patient that has a tumor or that has been determined to have a tumor. The patient-specific samples can be sequenced to provide a set of candidate peptide sequences for selection of neoantigens that have desired MHC presentation property and immunogenicity. The selection can be based on prediction results from the use of one or more neoantigen identification models, such as an MHC presentation model, an immunogenicity model, or a combination thereof. The selected neoantigens can be used to prepare pharmaceutically acceptable compositions or therapeutic agents, including immunogenic vaccines and T-cell therapies. The pharmaceutically acceptable compositions or therapeutic agents can be stored in a cold temperature for later distribution (if needed) and/or administered to the particular patient.

One or more candidate peptide sequences can be selected from a set of candidate peptide sequences based on results from an immunogenicity model described herein. For example, a selection can include identifying each of the subject-specific sets of candidate peptide sequences for which a predicted immunogenicity is meeting or exceeding a predefined immunogenicity threshold. It will be appreciated that outputs of the model may be on a different scale. For example, 500 nM may correspond to, for example, another value (e.g., 0.42) on a [0,1] scale.

A pharmaceutically acceptable composition may be developed and/or manufactured using one, a portion of, or all of the selected candidate peptide sequences. The composition may include mutant peptides corresponding to a single selected variant-coding sequence. The composition may include mutant peptides and/or mutant-peptide precursors corresponding to multiple selected candidate peptide sequences. A subset of peptide candidates (e.g., associated with the 5, 10, 15, 20, 30 or any number in between, highest presentation predictions) may be used for further precursor development.

Each of one, a portion of, or all of the mutant peptides in the composition can have, for example, a length of about 7 to about 40 amino acids (e.g., about any of 7, 8, 9, 10, 11, 12, 13, 14, 15, 17, 20, 22, 25, 30, 35, 40, 45, 50, 60 or 70 amino acids in length). In some embodiments, a length of each of one, a portion of, or all of the mutant peptides in the composition are within a predefined range (e.g., 8 to 11 amino acids, 8 to 12 amino acids or 8 to 15 amino acids). In some embodiments, each of one, a portion of, or all of the mutant peptides in the composition is about 8 to 10 amino acids in length. Each of one, a portion of, all of the mutant peptides in the compositions may be in its isolated form. Each of one, a portion of, of all of the mutant peptides in the composition may be a "long peptide" produced by adding one or more peptides to an end (or to each end) of the mutant peptide. Each of one, a portion of, or all of the mutant peptides in the composition may be tagged, may be a fusion protein, and/or may be a hybrid molecule.

A vaccine composition or a pharmaceutically acceptable composition may be developed and/or manufactured to include or by using one or more nucleic acids that encode—for each of one, more or all of the selected candidate peptide sequences—the peptide that includes or is composed by amino acids as identified in the candidate peptide sequences. The nucleic acid(s) can include DNA, RNA and/or mRNA. Given that any of multiple codons can encode a given amino acids, the codons may be selected to, for example, optimize or promote expression in a given type of organism. Such selection may be based on a frequency that each of multiple potential codons are used by the given type of organism, the translational efficiency of each of multiple potential codons in the given type of organism, and/or the given type of organism's degree of bias towards each of the multiple potential codons.

In some instances, the composition may include nucleic acids encoding the mutant peptide(s) or precursor of the mutant peptide(s) described above. The nucleic acid may include sequences flanking the sequence coding the mutant peptide (or precursor thereof). In some instances, the nucleic acid includes epitopes corresponding to more than one selected candidate peptide sequences. In some instances, the nucleic acid is DNA having a polynucleotide sequence encoding the mutant peptides or precursors described above.

In some instances, the nucleic acid is RNA. In some instances, the RNA is reverse transcribed from a DNA template having a polynucleotide sequence encoding the mutant peptides or precursors described above. In some instances, the RNA is mRNA. In some instances, the RNA is naked mRNA. In some instances, the RNA is modified mRNA (e.g., mRNA protected from degradation using protamine, mRNA containing modified 5'CAP structure, or mRNA containing modified nucleotides). In some embodiments, the RNA is single-stranded mRNA.

The composition may include cells comprising the mutant peptide and/or nucleic acid(s) encoding the mutant peptide described above. The composition may further comprise one or more suitable vectors and/or one or more delivery systems for the mutant peptide and/or nucleic acid(s) encoding the mutant peptide. In some instances, the cells comprising the mutant peptide and/or nucleic acids encoding the mutant peptide are non-human cells, for example, bacterial cells, protozoan cells, fungal cells, or non-human animal cells. In some instances, the cells comprising the mutant peptide and/or nucleic acids encoding the mutant peptide are human cells. In some instances, the human cells are immune cells. In some instances, the immune cells are antigen-presenting cells (APCs). In some instances, the APCs are professional APCs, such as macrophages, monocyte, dendritic cells, B cells, and microglia. In other instances, the professional APCs are macrophages or dendritic cells. In some instances, the APCs comprising the mutant peptide and/or nucleic acid sequence(s) encoding the mutant peptide are used as a cellular vaccine, thereby inducing a CD4+ or a CD8+ immune response. In other instances, the composition used as a cellular vaccine includes mutant peptide-specific T cells primed by APCs comprising the mutant peptide and/or nucleic acid sequence(s) encoding the mutant peptide.

The composition may include a pharmaceutically acceptable adjuvant and/or pharmaceutically acceptable excipient. Adjuvants refer to any substance for which admixture into a composition modifies an immune response to a mutant peptide. Adjuvants may be conjugated using, for example, an immune stimulation agent. Excipients can increase the molecular weight of a mutant peptide to increase activity or immunogenicity, confer stability, increase biological activity, and/or increase serum half-life.

The pharmaceutically acceptable composition may be a vaccine, which can include an individualized vaccine that is specific to (e.g., and potentially developed for) a subject. For example, an MHC sequence may have been identified using a sample from the subject, and the composition may be developed for and/or used to treat the subject.

The vaccine may be a nucleic acid vaccine. The nucleic acid can encode a mutant peptide or precursor of the mutant peptide. The nucleic acid vaccine may include sequences flanking the sequence coding the mutant peptide (or precursor thereof). In some instances, the nucleic acid vaccine includes epitopes corresponding to more than one selected candidate peptide sequences. In some instances, the nucleic acid vaccine is a DNA-based vaccine. In some instances, the nucleic acid vaccine is a RNA-based vaccine. In some instances, the RNA-based vaccine comprises mRNA. In some instances, the RNA-based vaccine comprises naked mRNA. In some instances, the RNA-based vaccine comprises modified mRNA (e.g., mRNA protected from degradation using protamine, mRNA containing modified 5'CAP structure, or mRNA containing modified nucleotides). In some embodiments, the RNA-based vaccine comprises single-stranded mRNA.

A nucleic-acid vaccine may include an individualized neoantigen specific therapy manufactured for a subject to be used as part of next-generation immunotherapy. The individualized vaccine may have been designed by first detecting mutant peptides in a sample of the subject and subsequently predicting, for each detected mutant peptide, whether and/or a degree to which the peptide will trigger an immunological response. Based on these predictions, a subset of the detected mutant peptides can be selected (e.g., a subset having at least 1, at least 2, at least 3, at least 5, at least 8, at least 10, at least 12, at least 15, at least 18, up to 40, up to 30, up to 25, up to 20, up to 18, up to 15 and/or up to 10 mutant peptides). For each selected mutant peptide, a synthetic mRNA sequence can be identified that codes for the mutant peptide. An mRNA vaccine may include mRNA (that encodes part or all a mutant peptide) complexed with lipids to form an mRNA-lipoplex. Administration of a vaccine that includes the mRNA-lipoplex can result in the mRNA stimulating TLR7 and TLR8, triggering T-cell activation by dendritic cells. Further, the administration can result in translation of mRNA into a mutant peptide, which can then bind to and be presented by MHC molecules and induce T-cell response.

The composition may include substantially pure mutant peptides, substantially pure precursors, and/or substantially pure nucleic acids encoding the mutant peptides or precursors thereof. The composition may include on more suitable vectors and/or one or more delivery systems to contain the mutant peptides, precursors thereof, and/or nucleic acids encoding the mutant peptides or precursors thereof. Suitable vectors and delivery systems include viral, such as systems based on adenovirus, vaccinia virus, retroviruses, herpes virus, adeno-associated virus or hybrids containing elements of more than one virus. Non-viral delivery systems include cationic lipids and cationic polymers (e.g., cationic liposomes). In some embodiments, physical delivery, such as with a 'gene-gun' may be used.

In certain embodiments, the RNA-based vaccine includes an RNA molecule including, in the 5' to 3' direction: (1) a 5' cap; (2) a 5' untranslated region (UTR); (3) a polynucleotide sequence encoding a secretory signal peptide; (4) a polynucleotide sequence encoding the one or more mutant peptides resulting from cancer-specific somatic mutations present in the tumor specimen; (5) a polynucleotide sequence encoding at least a portion of a transmembrane and cytoplasmic domain of a major histocompatibility complex (MHC) molecule; (6) a 3' UTR including: (a) a 3' untranslated region of an Amino-Terminal Enhancer of Split (AES) mRNA or a fragment thereof; and (b) non-coding RNA of a mitochondrially encoded 12S RNA or a fragment thereof; and (7) a poly(A) sequence. This example RNA molecule was also used in evaluating an example implementation of a prediction machine learning model, as discussed herein.

In certain embodiments, the RNA molecule further includes a polynucleotide sequence encoding an amino acid linker, wherein the polynucleotide sequences encoding the amino acid linker and a first of the one or more mutant peptides form a first linker-neoepitope module, and wherein the polynucleotide sequences forming the first linker-neoepitope module are between the polynucleotide sequence encoding the secretory signal peptide and the polynucleotide sequence encoding the at least a portion of the transmembrane and cytoplasmic domain of the MHC molecule in the 5' to 3' direction.

In certain embodiments, the RNA molecule further includes, in the 5' □3' direction: at least a second linker-epitope module, wherein the at least second linker-epitope module includes a polynucleotide sequence encoding an amino acid linker and a polynucleotide sequence encoding a neoepitope; wherein the polynucleotide sequences forming the second linker-neoepitope module are between the polynucleotide sequence encoding the neoepitope of the first linker-neoepitope module and the polynucleotide sequence encoding the at least portion of the transmembrane and cytoplasmic domain of the MHC molecule in the 5' to 3' direction; and wherein the neoepitope of the first linker-epitope module is different from the neoepitope of the second linker-epitope module. In certain embodiments, the RNA molecule includes 5 linker-epitope modules, wherein the 5 linker-epitope modules each encode a different neoepitope. In certain embodiments, the RNA molecule includes 10 linker-epitope modules, wherein the 10 linker-epitope modules each encode a different neoepitope. In certain embodiments, the RNA molecule includes 20 linker-epitope modules, wherein the 20 linker-epitope modules each encode a different neoepitope.

In certain embodiments, the RNA molecule further includes a second polynucleotide sequence encoding an amino acid linker, wherein the second polynucleotide sequence encoding the amino acid linker is between the polynucleotide sequence encoding the neoepitope that is most distal in the 3' direction, and the polynucleotide sequence encoding the at least portion of the transmembrane and cytoplasmic domain of the MHC molecule.

In certain embodiments, the 5' cap includes a D1 diastereomer of the structure:

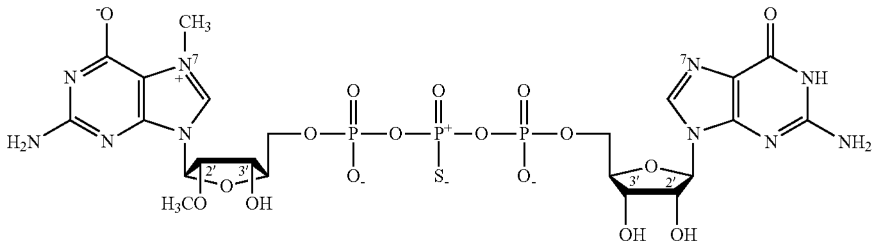

In some embodiments, mutant peptides described herein (e.g., including or consisting of an ordered set of amino acids as identified by candidate peptide sequences selected based on results from a machine-learning technique described herein) can be used for making mutant peptide specific therapeutics, such as antibody therapeutics. For example, the mutant peptides can be used to raise and/or identify antibodies specifically recognizing the mutant peptides. These antibodies can be used as therapeutics. Synthetic short peptides have been used to generate protein-reactive antibodies. An advantage of immunizing with synthetic peptides is that unlimited quantity of pure stable antigen can be used. This approach involves synthesizing the short peptide sequences, coupling them to a large carrier molecule, and immunizing a subject with the peptide-carrier molecule. The properties of antibodies are dependent on the primary sequence information. A good response to the desired peptide usually can be generated with careful selection of the sequence and coupling method. Most peptides can elicit a good response. An advantage of anti-peptide antibodies is that they can be prepared immediately after determining the amino acid sequence of a mutant peptide and the particular regions of a protein can be targeted specifically for antibody production. Selecting mutant peptides for which an immunogenicity model predicted immunogenicity and/or screening for the same can lead to a high chance that the resulting antibody will recognize the native protein in the tumor setting. A mutant peptide may be, for example, 15 or fewer, 18 or fewer or 20 or fewer, 25 or fewer, 30 or fewer, 35 or fewer, 40 or fewer, 50 or fewer, 60 or fewer, 70 or fewer, 85 or fewer, 100 or fewer, 110 or fewer residues. A mutant peptide may be, for example, 9 or more, 10 or more, 15 or more, 20 or more, 25 or more, 30 or more, 50 or more, or 70 or more residues. Shorter peptides can improve antibody production.

Peptide-carrier protein coupling can be used to facilitate production of high titer antibodies. A coupling method can include, for example, site-directed coupling and/or a technique that relies on the reactive functional groups in amino acids, such as —NH2, —COOH, —SH, and phenolic —OH. Any suitable method used in anti-peptide antibody production can be utilized with the mutant peptides identified by the methods of the present invention. Two such known methods are the Multiple Antigenic Peptide system (MAPs) and the Lipid Core Peptides (LCP method). An advantage of MAPs is that the conjugation method is not necessary. No carrier protein or linkage bond is introduced into the immunized host. One disadvantage is that the purity of the peptide is more difficult to control. In addition, MAPs can bypass the immune response system in some hosts. The LCP method is known to provide higher titers than other anti-peptide vaccine systems and thus can be advantageous.

Also provided herein are isolated MHC/peptide complexes comprising one or more mutant peptides identified using a technique disclosed herein. Such MHC/peptide complexes can be used, for example, for identifying antibodies, soluble TCRs, or TCR analogs. One type of these antibodies has been termed TCR mimics, as they are antibodies that hind peptides from tumor associated antigens in the context of specific HLA environments. This type of antibody has been shown to mediate the lysis of cells expressing the complex on their surface as well as to protect mice from implanted cancer cells lines that express the complex (see, for example, Vaughan P. Wittman et al., Antibody targeting to a class I MHC-peptide epitope promotes tumor cell death, 177 J. of Immunol., 4187-4195 (2006)). One advantage of TCR mimics as IgG mAbs is that affinity maturation can be performed and the molecules are coupled with immune effector functions through the present Fc domain. These antibodies can also be used to target therapeutic molecules to tumors, such as toxins, cytokines, or drug products.

Other types of molecules may be developed using mutant peptides such as those selected using the methods of the present invention using non-hybridoma based antibody production or production of binding competent antibody fragments such as anti-peptide Fab molecules on bacteriophage. These fragments can also be conjugated to other therapeutic molecules for tumor delivery such as anti-peptide MHC Fab-immunotoxin conjugates, anti-peptide MHC Fab-cytokine conjugates and anti-peptide MHC Fab-drug conjugates.

IX. Methods of Treatment Including Immunogenic Vaccines or T Cells

Some embodiments provide methods of treatment including a vaccine, which can be an immunogenic vaccine. In some embodiments, a method of treatment for disease (such as cancer) is provided, which may include administering to an individual an effective amount of a composition described herein, a mutant peptide identified using a technique disclosed herein, a precursor thereof, or nucleic acids encoding a mutant peptide (or precursor) identified using a technique described herein.

In some embodiments, a method of treatment for a disease (such as cancer) is provided. The method may include collecting a sample (e.g., a blood sample) from a subject. T cells can be isolated and stimulated. The isolation can be performed using, for example, density gradient sedimentation (e.g., and centrifugation), immunomagnetic selection, and/or antibody-complex filtering. The stimulation may include, for example, antigen-independent stimulation, which may use a mitogen (e.g., PHA or Con A) or anti-CD3 antibodies (e.g., to bind to CD3 and activate the T-cell receptor complex) and anti-CD28 antibodies (e.g., to bind to CD28 and stimulate T cells). One or more mutant peptides can be (or may have been) selected to use in the treatment of the subject (e.g., based on results produced by an immunogenicity model corresponding to predictions as to whether to what extent each of set of mutant peptides would trigger immunogenicity in the individual, in accordance with one or more techniques disclosed herein). The one or more mutant peptides may have been selected based on a technique disclosed herein that includes identifying and processing one or more sequence representations associated with the subject (e.g., a representation of: an MHC sequence, a set of candidate peptide sequences). The one or more sequences may have been detected using the sample from which the T cells were isolated or a different sample.

In some instances, a method of treatment for a disease (such as cancer) is provided, which may include administering to an individual a composition that includes one or more mutant peptides (or one or more precursors thereof) in an amount effective to, for example, prime, activate and expand T cells in vivo.

In some embodiments, a method of treatment for a disease (such as cancer) is provided, which may include administering to an individual an effective amount of a composition including a precursor of a mutant peptide selected using a technique described herein. In some embodiments, an immunogenic vaccine may include a pharmaceutically acceptable mutant peptide selected using a technique described herein. In some embodiments, an immunogenic vaccine may include a pharmaceutically acceptable precursor to a mutant peptide selected using a technique described herein (such as a protein, peptide, DNA and/or RNA). In some embodiments, a method of treatment for a disease (such as cancer) is provided, which may include administering to an individual an effective amount of an antibody specifically recognizing a mutant peptide selected using a technique described herein. In some embodiments, a method of treatment for a disease (such as cancer) is provided, which may include administering to an individual an effective amount of a soluble TCR or TCR analog specifically recognizing a mutant peptide selected using a technique described herein.

In some embodiments, the cancer is any one of: carcinoma, lymphoma, blastema, sarcoma, leukemia, squamous cell cancer, lung cancer (including small cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, melanoma, endometrial or uterine carcinoma, salivary gland carcinoma, kidney or renal cancer, liver cancer, prostate cancer, vulval cancer, thyroid cancer, hepatic carcinoma, head and neck cancer, colorectal cancer, rectal cancer, soft-tissue sarcoma, Kaposi's sarcoma, B-cell lymphoma (including low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's macroglobulinemia), chronic lymphocytic leukemia (CLL), acute lymphoblastic leukemia (ALL), myeloma, Hairy cell leukemia, chronic myeloblasts leukemia, and post-transplant lymphoproliferative disorder (PTLD), as well as abnormal vascular proliferation associated with phakomatoses, edema (such as that associated with brain tumors), and Meigs' syndrome.

Embodiments disclosed herein can including identifying part or all of and/or implementing part or all of an individualized-medicine strategy. For example, one or more mutant peptides may be selected for use in a vaccine by: determining an MHC sequence and/or a set of candidate peptide sequences using a sample from an individual; and processing representations of the MHC sequence and the candidate peptide sequences using an immunogenicity model disclosed herein (e.g., a neural network-based machine learning model). The one or more mutant peptides (and/or precursors thereof) may then be administered to the same individual.

In some embodiments, a method of treating a disease (such as cancer) in an individual is provided that includes: a) identifying a one or more mutant peptides in the individual (e.g., based on results produced by an immunogenicity model corresponding to predictions as to whether to what extent each of set of mutant peptides would be immunogenic, in accordance with one or more techniques disclosed herein); b) synthesizing the identified mutant peptide(s) or one or more precursors of the mutant peptide(s) or nucleic acid(s) (e.g., polynucleotides such as DNA or RNA) encoding the identified peptide(s) or peptide precursor(s); and c) administering the mutant peptide(s), mutant-peptide precursor(s) or nucleic acid(s) to the individual.

In some embodiments, a method of treating a disease (such as cancer) in an individual is provided that includes: a) identifying a one or more mutant peptides in the individual (e.g., based on results produced by an immunogenicity model corresponding to predictions as to whether to what extent each of set of mutant peptides would be immunogenic, in accordance with one or more techniques disclosed herein); b) identifying a set of nucleic acids (e.g., polynucleotides such as DNA or RNA) that encode the identified mutant peptide(s) or one or more precursors of the mutant peptide(s); c) synthesizing the set of nucleic acids; and d) administering the set of nucleic acids to the individual.

In some embodiments, a method of treating a disease (such as cancer) in an individual is provided that includes: a) identifying a one or more mutant peptides in the individual (e.g., based on results produced by an immunogenicity model corresponding to predictions as to whether to what extent each of set of mutant peptides would trigger immunogenicity in the individual, in accordance with one or more techniques disclosed herein); b) producing an antibody specifically recognizing the mutant peptide; and c) administering the peptide to the individual.

The methods provided herein can be used to treat an individual (e.g., human) who has been diagnosed with or is suspected of having cancer. In some embodiments, an individual may be a human. In some embodiments, an individual may be at least about any of 18, 20, 25, 30, 35, 40, 45, 50, 55, 60, 65, 70, 75, 80, or 85 years old. In some embodiments, an individual may be a male. In some embodiments, an individual may be a female. In some embodiments, an individual may have refused surgery. In some embodiments, an individual may be medically inoperable. In some embodiments, an individual may be at a clinical stage of Ta, Tis, T1, T2, T3a, T3b, or T4. In some embodiments, a cancer may be recurrent. In some embodiments, an individual may be a human who exhibits one or more symptoms associated with cancer. In some of embodiments, an individual may be genetically or otherwise predisposed (e.g., having a risk factor) to developing cancer.

The methods provided herein may be practiced in an adjuvant setting. In some embodiments, the method is practiced in a neoadjuvant setting, i.e., the method may be carried out before the primary/definitive therapy. In some embodiments, the method is used to treat an individual who has previously been treated. Any of the methods of treatment provided herein may be used to treat an individual who has not previously been treated. In some embodiments, the method is used as a first-line therapy. In some embodiments, the method is used as a second-line therapy.

In some embodiments, there is provided a method of reducing incidence or burden of preexisting cancer tumor metastasis (such as pulmonary metastasis or metastasis to the lymph node) in an individual, comprising administering to the individual an effective amount of a composition disclosed herein. In some embodiments, there is provided a method of prolonging time to disease progression of cancer in an individual, comprising administering to the individual an effective amount of a composition disclosed herein. In some embodiments, there is provided a method of prolonging survival of an individual having cancer, comprising administering to the individual an effective amount of a composition disclosed herein.

In some embodiments, at least one or more chemotherapeutic agents may be administered in addition to the composition disclosed herein. In some embodiments, the one or more chemotherapeutic agents may (but not necessarily) belong to different classes of chemotherapeutic agents.

In some embodiments, there is provided a method of treating a disease (such as cancer) in an individual, comprising administering: a) a vaccine disclosed herein (e.g., that includes a mutant peptide selected based on a machine-learning technique disclosed herein or a precursor thereof), and b) an immunomodulator. In some embodiments, there is provided a method of treating a disease (such as cancer) in an individual, comprising administering: a) a vaccine disclosed herein (e.g., that includes a mutant peptide selected based on a machine-learning technique disclosed herein or a precursor thereof), and b) an antagonist of a checkpoint protein. In some embodiments, there is provided a method of treating a disease (such as cancer) in an individual, comprising administering: a) a vaccine disclosed herein (e.g., that includes a mutant peptide selected based on a machine-learning technique disclosed herein or a precursor thereof), and b) an antagonist of programmed cell death 1 (PD-1), such as anti-PD-1. In some embodiments, there is provided a method of treating a disease (such as cancer) in an individual, comprising administering: a) a vaccine disclosed herein (e.g., that includes a mutant peptide selected based on a machine-learning technique disclosed herein or a precursor thereof), and b) an antagonist of programmed death-ligand 1 (PD-L1), such as anti-PD-L1. In some embodiments, there is provided a method of treating a disease (such as cancer) in an individual, comprising administering: a) a vaccine disclosed herein (e.g., that includes a mutant peptide selected based on a machine-learning technique disclosed herein or a precursor thereof), and b) an antagonist of cytotoxic T-lymphocyte-associated protein 4 (CTLA-4), such as anti-CTLA-4.

It will be appreciated that various disclosures refer to use of amino-acid sequences. Nucleic-acid sequences may additionally or alternatively be used. For example, a disease-specific sample may be sequenced to identify a set of nucleic-acid sequence that are not present in a corresponding non-disease-specific sample (e.g., from a same subject or different subject). Similarly, a nucleic-acid sequence of an MHC molecule and/or T-cell receptor may further be identified. Representations of each of a nucleic-acid disease-specific nucleic-acid sequence and of an MHC molecule (or of a T-cell receptor) may be processed by a machine learning model such as an attention-based model as described herein (e.g., and potentially having been trained using representations of nucleic-acid sequences).

X. Computer-Implemented System

Figure 8:
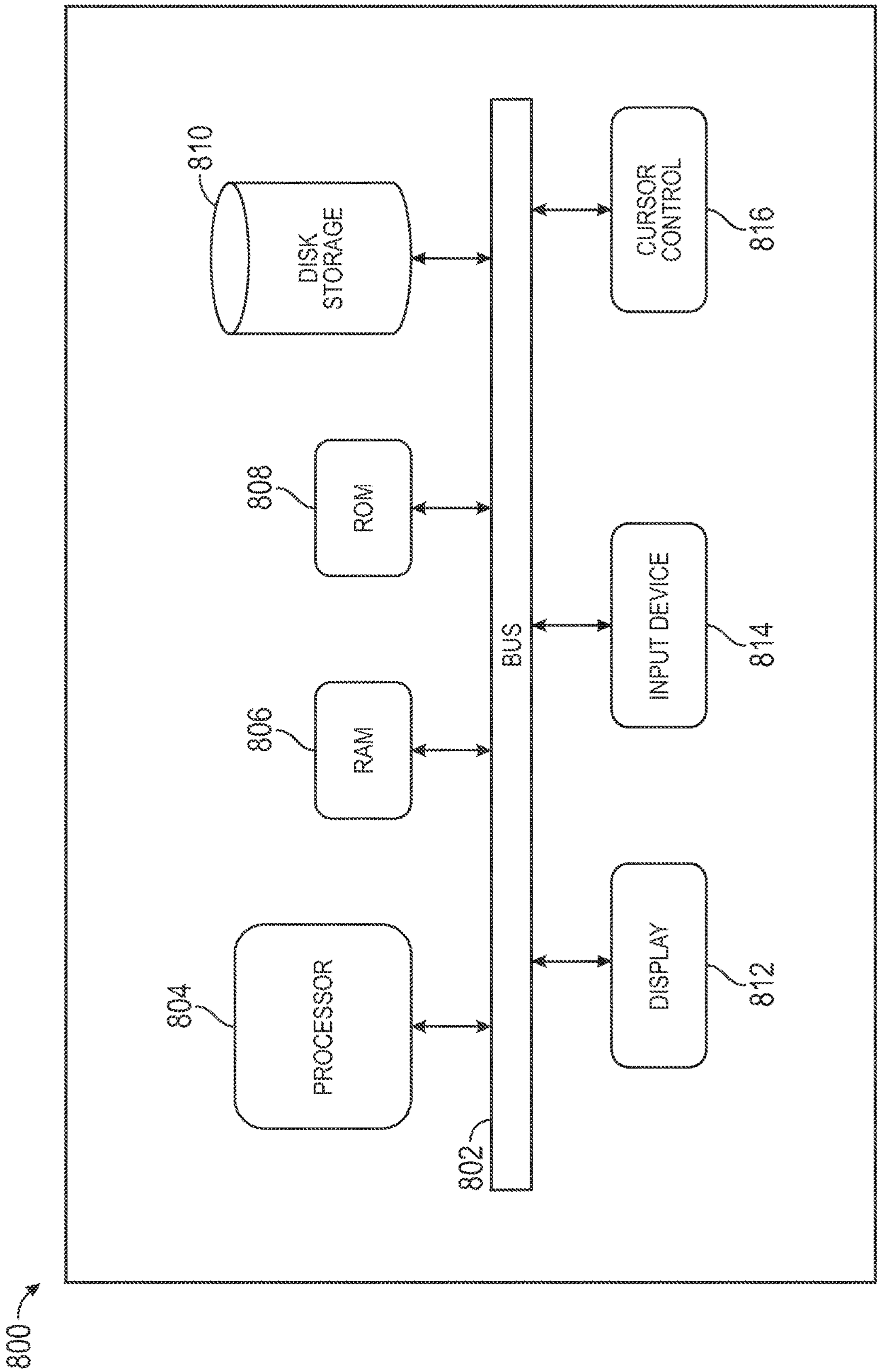
FIG. 8 is a block diagram of examples illustrating a computer system configure to perform methods provided herein, in accordance with various embodiments.

In various embodiments, any methods for predicting immunogenicity of candidate peptide sequences or as exemplified in workflow 100 in FIG. 1A, workflow 170 in FIG. 1B, workflow 200 in FIG. 2, method 600 in FIG. 6, or method 700 in FIG. 7 can be implemented via software, hardware, firmware, or a combination thereof, such as described in FIG. 8.

FIG. 8 is a block diagram illustrating a computer system 800 upon which embodiments of the present teachings may be implemented in accordance with various embodiments. In various embodiments of the present teachings, computer system 800 can include a bus 802 or other communication mechanism for communicating information and a processor 804 coupled with bus 802 for processing information. In various embodiments, computer system 800 can also include a memory, which can be a random-access memory (RAM) 806 or other dynamic storage device, coupled to bus 802 for determining instructions to be executed by processor 804. Memory can also be used for storing temporary variables or other intermediate information during execution of instructions to be executed by processor 804. In various embodiments, computer system 800 can further include a read only memory (ROM) 808 or other static storage device coupled to bus 802 for storing static information and instructions for processor 804. A storage device 810 (e.g., disk storage device), such as a magnetic disk or optical disk, can be provided and coupled to bus 802 for storing information and instructions.

In various embodiments, processor 804 can be coupled via bus 802 to a display 812, such as a cathode ray tube (CRT) or liquid crystal display (LCD), for displaying information to a computer user. An input device 814, including alphanumeric and other keys, can be coupled to bus 802 for communication of information and command selections to processor 804. Another type of user input device is a cursor control, such as a mouse, a trackball or cursor direction keys for communicating direction information and command selections to processor 804 and for controlling cursor movement on display 812.

Consistent with certain implementations of the present teachings, results can be provided by computer system 800 in response to processor 804 executing one or more sequences of one or more instructions contained in memory 806. Such instructions can be read into memory 806 from another computer-readable medium or computer-readable storage medium, such as storage device 810. Execution of the sequences of instructions contained in memory 806 can cause processor 804 to perform the processes described herein. Alternatively, hard-wired circuitry can be used in place of or in combination with software instructions to implement the present teachings. Thus, implementations of the present teachings are not limited to any specific combination of hardware circuitry and software.

The term "computer-readable medium" (e.g., data store, data storage, etc.) or "computer-readable storage medium" as used herein refers to any media that participates in providing instructions to processor 804 for execution. Such a medium can take many forms, including but not limited to, non-volatile media, volatile media, and transmission media. Examples of non-volatile media can include, but are not limited to, dynamic memory, such as memory 806. Examples of transmission media can include, but are not limited to, coaxial cables, copper wire, and fiber optics, including the wires that comprise bus 802.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, another memory chip or cartridge, or any other tangible medium from which a computer can read.

In addition to computer-readable medium, instructions or data can be provided as signals on transmission media included in a communications apparatus or system to provide sequences of one or more instructions to processor 804 of computer system 800 for execution. For example, a communication apparatus may include a transceiver having signals indicative of instructions and data. The instructions and data are configured to cause one or more processors to implement the functions outlined in the disclosure herein. Representative examples of data communications transmission connections can include, but are not limited to, telephone modem connections, wide area networks (WAN), local area networks (LAN), infrared data connections, NFC connections, etc.

It should be appreciated that the methodologies described herein, flow charts, diagrams and accompanying disclosure can be implemented using computer system 800 as a standalone device or on a distributed network or shared computer processing resources such as a cloud computing network.

The methodologies described herein may be implemented by various means depending upon the application. For example, these methodologies may be implemented in hardware, firmware, software, or any combination thereof. For a hardware implementation, the processing unit may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

In various embodiments, the methods of the present teachings may be implemented as firmware and/or a software program and applications written in conventional programming languages such as C, C++, Python, etc. If implemented as firmware and/or software, the embodiments described herein can be implemented on a non-transitory computer-readable medium in which a program is stored for causing a computer to perform the methods described above. It should be understood that the various engines described herein can be provided on a computer system, such as computer system 800, whereby a processor would execute the analyses and determinations provided by these engines, subject to instructions provided by any one of, or a combination of, memory components 806, 808, and 810 and user input provided via an input device.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

In describing the various embodiments, the specification may have presented a method and/or process as a particular sequence of steps. However, to the extent that the method or process does not rely on the particular order of steps set forth herein, the method or process should not be limited to the particular sequence of steps described, and one skilled in the art can readily appreciate that the sequences may be varied and still remain within the spirit and scope of the various embodiments.

XI. Recitation of Embodiments

Embodiment 1. A method comprising: receiving a set of candidate peptide sequences, each candidate peptide sequence in the set having a major histocompatibility complex (MHC) presentation score meeting a pre-set criterion, wherein the set of candidate peptide sequences is associated with a diseased sample of a subject and wherein the MHC presentation score indicates a likelihood that a corresponding candidate peptide sequence in the set is presented by an MHC protein on a cell surface of the diseased sample; identifying a corresponding MHC peptide sequence associated with each candidate peptide sequence in the set; generating immunogenicity input vectors from the set of candidate peptide sequences by processing a representation of each candidate peptide sequence in the set of candidate peptide sequences and a representation of the corresponding MHC peptide sequence for each candidate peptide sequence in the set; inputting the immunogenicity input vectors into an immunogenicity model to generate predictions of whether a candidate peptide sequence in the set is immunogenic, a likelihood that a candidate peptide sequence in the set is immunogenic, or a combination thereof; and returning an output comprising the predictions.

Embodiment 2. The method of embodiment 1, further comprising: generating predictions for a set comprising a plurality of candidate peptide sequences.

Embodiment 3. The method of embodiment 2, further comprising: generating a report that ranks the plurality of candidate peptide sequences based on their predicted likelihood of being immunogenic.

Embodiment 4. The method of any one of embodiments 1-3, further comprising: determining an MHC presentation score for each candidate peptide sequence of the set.

Embodiment 5. The method of embodiment 4, wherein determining an MHC presentation score comprises: receiving an initial set of candidate peptide sequences, wherein each candidate peptide sequence of the initial set is associated with the diseased sample; identifying a corresponding MHC peptide sequence for each candidate peptide sequence of the initial set; generating a presentation input vector by processing, for each of the initial set of candidate peptide sequences, a representation of each candidate peptide sequence in the initial set and a representation of the corresponding MHC peptide sequence for each candidate peptide sequence in the initial set; inputting the presentation input vector into a presentation model to determine an MHC presentation score for each candidate peptide sequence in the initial set; and selecting the set of candidate peptide sequences from the initial set of candidate peptide sequences based on the MHC presentation score.

Embodiment 6. The method of any one of embodiments 1-5, wherein the pre-set criterion is a pre-defined threshold or a top-ranked number.

Embodiment 7. The method of any one of embodiments 1-6, wherein the corresponding MHC peptide sequence for a candidate peptide sequence of the set comprises an abbreviated pseudo-sequence of the MHC peptide sequence of the subject.

Embodiment 8. The method of any one of embodiments 1-7, wherein a candidate peptide sequence of the set comprises a N-terminus sequence of the candidate peptide sequence and an epitope of the candidate peptide sequence.

Embodiment 9. The method of any one of embodiments 1-8, wherein a candidate peptide sequence of the set has one or more mutations compared to a corresponding reference sequence associated with a healthy sample of the subject.

Embodiment 10. The method of any one of embodiments 1-9, wherein the diseased sample is a tumor sample or a sample from a subject that has been determined to have a tumor.

Embodiment 11. The method of any one of embodiments 1-10, wherein the immunogenicity model is a transformer-based model having a plurality of layers.

Embodiment 12. The method of any one of embodiments 1-11, wherein the immunogenicity model was initially trained with unlabeled peptide sequences from a protein database.

Embodiment 13. The method of embodiment 12, wherein the immunogenicity model was further trained after initial training with an MHC-I binding dataset comprising peptide sequences labeled with MHC-I binding.

Embodiment 14. The method of embodiment 13, wherein the immunogenicity model was further trained after initial training with an MHC-II binding dataset comprising peptide sequences labeled with MHC-II binding.

Embodiment 15. The method of embodiment 14, wherein the immunogenicity model was further trained after initial training with an immunogenicity dataset comprising peptide sequences labeled with immunogenicity.

Embodiment 16. The method of any one of embodiments 13-15, wherein during further training, the immunogenicity model was trained by unfreezing different ones of a plurality of layers of the immunogenicity model in different epochs, training different ones of the layers with different learning rates, changing learning rates with a rising and falling phase between epochs, or any combination thereof.

Embodiment 17. The method of embodiment 16, wherein the immunogenicity model was trained by unfreezing the last two layers of the immunogenicity model followed by unfreezing other layers of the immunogenicity model.

Embodiment 18. The method of embodiment 16, wherein the immunogenicity model was trained by changing learning rates with a non-linear rising and falling phase.

Embodiment 19. The method of any one of embodiments 1-18, further comprising: preparing a vaccine composition comprising a candidate peptide sequence that is selected from the set based on the predictions indicating that the candidate peptide sequence is immunogenic.

Embodiment 20. The method of embodiment 19, further comprising: providing a treatment recommendation to the subject, wherein the treatment recommendation comprises administering the vaccine composition to the subject.

Embodiment 21. The method of any one of embodiments 1-20, further comprising: selecting an immunogenic peptide from the set based on the predictions; and preparing a therapeutic composition comprising a therapeutic agent that targets or comprises the immunogenic peptide.

Embodiment 22. The method of embodiment 21, further comprising: providing a treatment recommendation to the subject, wherein the treatment recommendation comprises administering the therapeutic composition to the subject.

Embodiment 23. The method of any one of embodiments 1-22, wherein the corresponding MHC peptide sequence associated with each candidate peptide sequence in the set is an MHC-I peptide sequence or an MHC-H peptide sequence.

Embodiment 24. A method comprising: receiving a candidate peptide sequence having a major histocompatibility complex (MHC) presentation score meeting a pre-set criterion, wherein the candidate peptide sequence is associated with a diseased sample of a subject, and wherein the MHC presentation score indicates a likelihood that the candidate peptide sequence is presented by a MHC protein on a cell surface of the diseased sample; identifying a corresponding MHC peptide sequence associated with the candidate peptide sequence; generating an input vector for the candidate peptide sequence by processing a representation of the candidate peptide sequence and a representation of the corresponding MHC peptide sequence; inputting the input vector generated into an immunogenicity model to generate a prediction of whether the candidate peptide sequence is immunogenic, a likelihood that the candidate peptide sequence is immunogenic, or a combination thereof; and returning an output comprising the prediction.

Embodiment 25. The method of embodiment 24, further comprising: generating predictions for a data set comprising a plurality of candidate peptide sequences.

Embodiment 26. The method of embodiment 25, further comprising: generating a report that ranks the plurality of candidate peptide sequences based on their predicted likelihood of being immunogenic.

Embodiment 27. A vaccine composition comprising: one or more peptides; a plurality of nucleic acids that encode the one or more peptides; a plurality of cells expressing the one or more peptides, or a combination thereof, wherein the one or more peptides were selected from the set of candidate peptide sequences based on the predictions generated by the method in accordance with any one of embodiments 1-26.

Embodiment 28. The vaccine composition of embodiment 27, wherein the plurality of nucleic acids comprises RNA.

Embodiment 29. A method of manufacturing a vaccine comprising: producing a vaccine comprising: one or more peptides, a plurality of nucleic acids that encode the one or more peptides, a plurality of cells expressing the one or more peptides, or a combination thereof, wherein the one or more peptides were selected from the set of candidate peptide sequences based on the predictions generated by the method in accordance with any one of embodiments 1-26.

Embodiment 30. A genetically engineered T cell composition comprising: one or more peptides, a plurality of nucleic acids that encode the one or more peptides, an antibody or an inhibitor that targets the one or more peptides, a plurality of nucleic acids that encode the antibody that targets the one or more peptides, or a combination thereof; wherein the one or more peptides were selected from the set of candidate peptide sequences based on the predictions generated by the method in accordance with any one of embodiments 1-26.

Embodiment 31. A pharmaceutical composition comprising one or more peptides having been selected from the set of candidate peptide sequences based on the predictions generated by the method in accordance with any one of embodiments 1-26.

Embodiment 32. A pharmaceutical composition comprising a nucleic acid sequence that encodes one or more peptides having been selected from the set of candidate peptide sequences based on the predictions generated by the method in accordance with any one of embodiments 1-26.

Embodiment 33. An immunogenic peptide identified based on the predictions generated by the method in accordance with any one of embodiments 1-26.

Embodiment 34. A nucleic acid sequence identified based on the predictions generated by the method in accordance with any one of embodiments 1-26.

Embodiment 35. A method of treating a subject comprising administering one or more peptides, one or more pharmaceutical compositions, or one or more nucleic acid sequences identified based on the predictions generated by the method in accordance with any one of embodiments 1-26.

Embodiment 36. A system comprising: one or more data processors; and a non-transitory computer readable storage medium containing instructions which, when executed on the one or more data processors, cause the one or more data processors to perform part or all of the method in accordance with any one of embodiments 1-26.

Embodiment 37. A computer-program product tangibly embodied in a non-transitory machine-readable storage medium, including instructions configured to cause one or more data processors to perform part or all of the method in accordance with any one of embodiments 1-26.

XII. Additional Considerations

The headers and subheaders between sections and subsections of this document are included solely for the purpose of improving readability and do not imply that features cannot be combined across sections and subsection. Accordingly, sections and subsections do not describe separate embodiments.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

The invention claimed is:

1. A method comprising:

training an immunogenicity model by:

training, in a first stage, the immunogenicity model using a training peptide-MHC binding dataset; and training, in a second stage, the immunogenicity model using a training immunogenicity dataset comprising one or more peptide sequences labeled indicative of assay-derived immune responses;

receiving a set of candidate peptide sequences, each candidate peptide sequence in the set having a major histocompatibility complex (MHC) presentation score meeting a pre-set criterion, wherein the set of candidate peptide sequences is associated with a diseased sample of a subject; and wherein the MHC presentation score indicates a likelihood that a corresponding candidate peptide sequence in the set is presented by an MHC protein on a cell surface of the diseased sample;

identifying a corresponding MHC peptide sequence associated with each candidate peptide sequence in the set;

generating immunogenicity input vectors from the set of candidate peptide sequences by processing a representation of each candidate peptide sequence in the set of candidate peptide sequences; and a representation of the corresponding MHC peptide sequence for each candidate peptide sequence in the set;

inputting the immunogenicity input vectors into the immunogenicity model to generate predictions of whether a candidate peptide sequence in the set is immunogenic, a likelihood that a candidate peptide sequence in the set is immunogenic, or a combination thereof; and returning an output comprising the predictions.

2. The method of claim 1, further comprising:

generating predictions for a set comprising a plurality of candidate peptide sequences; and generating a report that ranks the plurality of candidate peptide sequences based on their predicted likelihood of being immunogenic.

3. The method of claim 1, further comprising:

determining an MHC presentation score for each candidate peptide sequence of the set.

4. The method of claim 3, wherein determining an MHC presentation score comprises:

receiving an initial set of candidate peptide sequences, wherein each candidate peptide sequence of the initial set is associated with the diseased sample;

identifying a corresponding MHC peptide sequence for each candidate peptide sequence of the initial set;

generating a presentation input vector by processing, for each of the initial set of candidate peptide sequences, a representation of each candidate peptide sequence in the initial set and a representation of the corresponding MHC peptide sequence for each candidate peptide sequence in the initial set;

inputting the presentation input vector into a presentation model to determine an MHC presentation score for each candidate peptide sequence in the initial set; and selecting the set of candidate peptide sequences from the initial set of candidate peptide sequences based on the MHC presentation score.

5. The method of claim 1, wherein the pre-set criterion is a pre-defined threshold or a top-ranked number.

6. The method of claim 1, wherein the corresponding MHC peptide sequence for a candidate peptide sequence of the set comprises an abbreviated pseudo-sequence of the MHC peptide sequence of the subject.

7. The method of claim 1, wherein at least one of:

a candidate peptide sequence of the set comprises a N-terminus sequence of the candidate peptide sequence and an epitope of the candidate peptide sequence, or one or more mutations compared to a corresponding reference sequence associated with a healthy sample of the subject.

8. The method of claim 1, wherein the diseased sample is a tumor sample or a sample from a subject that has been determined to have a tumor.

9. The method of claim 1, wherein the immunogenicity model is a transformer-based model having a plurality of layers.

10. The method of claim 1, wherein the immunogenicity model was initially trained with unlabeled peptide sequences from a protein database.

11. The method of claim 10, wherein the immunogenicity model is trained in the first stage with an MHC-I binding dataset comprising peptide sequences labeled with MHC-I binding.

12. The method of claim 11, wherein the immunogenicity model is trained in the first stage with an MHC-II binding dataset comprising peptide sequences labeled with MHC-II binding.

13. The method of claim 11, wherein during further training, the immunogenicity model was trained by unfreezing different ones of a plurality of layers of the immunogenicity model in different epochs, training different ones of the of the plurality of layers with different learning rates, changing learning rates with a rising and falling phase between epochs, or any combination thereof.

14. The method of claim 13, wherein the immunogenicity model was trained by at least one of:

unfreezing a last two layers of the immunogenicity model followed by unfreezing other layers of the immunogenicity model; or changing learning rates with a non-linear rising and falling phase.

15. The method of claim 1, further comprising:

preparing a vaccine composition comprising a candidate peptide sequence that is selected from the set based on the predictions indicating that the candidate peptide sequence is immunogenic; and providing a treatment recommendation to the subject, wherein the treatment recommendation comprises administering the vaccine composition to the subject.

16. The method of claim 1, further comprising:

selecting an immunogenic peptide from the set based on the predictions;

preparing a therapeutic composition comprising a therapeutic agent that targets or comprises the immunogenic peptide; and providing a treatment recommendation to the subject, wherein the treatment recommendation comprises administering the therapeutic composition to the subject.

17. The method of claim 1, wherein the corresponding MHC peptide sequence associated with each candidate peptide sequence in the set is an MHC-I peptide sequence or an MHC-II peptide sequence.

18. The method of claim 1, further comprising administering, to the subject, a vaccine composition comprising a candidate peptide sequence that is selected from the set based on the predictions indicating that the candidate peptide sequence is immunogenic.

19. A system comprising:

one or more data processors; and a non-transitory computer readable storage medium containing instructions which, when executed on the one or more data processors, cause the one or more data processors to:

train an immunogenicity model by:

training, in a first stage, the immunogenicity model using a training peptide-MHC binding dataset; and training, in a second stage, the immunogenicity model using a training immunogenicity dataset comprising one or more peptide sequences labeled indicative of assay-derived immune responses;

receive a set of candidate peptide sequences, each candidate peptide sequence in the set having a major histocompatibility complex (MHC) presentation score meeting a pre-set criterion, wherein the set of candidate peptide sequences is associated with a diseased sample of a subject; and wherein the MHC presentation score indicates a likelihood that a corresponding candidate peptide sequence in the set is presented by an MHC protein on a cell surface of the diseased sample;

identify a corresponding MHC peptide sequence associated with each candidate peptide sequence in the set;

generate immunogenicity input vectors from the set of candidate peptide sequences by processing:

a representation of each candidate peptide sequence in the set of candidate peptide sequences; and a representation of the corresponding MHC peptide sequence for each candidate peptide sequence in the set;

input the immunogenicity input vectors into the immunogenicity model to generate predictions of whether a candidate peptide sequence in the set is immunogenic, a likelihood that a candidate peptide sequence in the set is immunogenic, or a combination thereof; and return an output comprising the predictions.

20. A computer-program product tangibly embodied in a non-transitory machine-readable storage medium, including instructions configured to cause one or more data processors to perform a method comprising:

training an immunogenicity model by:

training, in a first stage, the immunogenicity model using a training peptide-MHC binding dataset; and training, in a second stage, the immunogenicity model using a training immunogenicity dataset comprising one or more peptide sequences labeled indicative of assay-derived immune responses;

receiving a set of candidate peptide sequences, each candidate peptide sequence in the set having a major histocompatibility complex (MHC) presentation score meeting a pre-set criterion, wherein the set of candidate peptide sequences is associated with a diseased sample of a subject; and wherein the MHC presentation score indicates a likelihood that a corresponding candidate peptide sequence in the set is presented by an MHC protein on a cell surface of the diseased sample;

identifying a corresponding MHC peptide sequence associated with each candidate peptide sequence in the set;

generating immunogenicity input vectors from the set of candidate peptide sequences by processing:

a representation of each candidate peptide sequence in the set of candidate peptide sequences; and a representation of the corresponding MHC peptide sequence for each candidate peptide sequence in the set;

inputting the immunogenicity input vectors into the immunogenicity model to generate predictions of whether a candidate peptide sequence in the set is immunogenic, a likelihood that a candidate peptide sequence in the set is immunogenic, or a combination thereof; and returning an output comprising the predictions.

* * * * *